US011357845B2

(12) United States Patent
Shen et al.

(10) Patent No.: US 11,357,845 B2
(45) Date of Patent: Jun. 14, 2022

(54) **PROTEIN ANTIGENS FOR VACCINATING AGAINST NONTYPEABLE *HAEMOPHILUS INFLUENZAE***

(71) Applicants: THE TRUSTEES OF THE UNIVERSITY OF PENNSYLVANIA, Philadelphia, PA (US); University of Mississippi Medical Center, Jackson, MS (US)

(72) Inventors: Hao Shen, Philadelphia, PA (US); Brian Akerley, Ridgeland, MS (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 16/922,463

(22) Filed: Jul. 7, 2020

(65) Prior Publication Data

US 2021/0008193 A1 Jan. 14, 2021

Related U.S. Application Data

(60) Provisional application No. 62/871,433, filed on Jul. 8, 2019.

(51) Int. Cl.
| | |
|---|---|
| *A61K 39/39* | (2006.01) |
| *A61K 39/102* | (2006.01) |
| *A61P 31/04* | (2006.01) |
| *A61K 39/00* | (2006.01) |

(52) U.S. Cl.
CPC ............ *A61K 39/102* (2013.01); *A61K 39/39* (2013.01); *A61P 31/04* (2018.01); *A61K 2039/57* (2013.01)

(58) Field of Classification Search
None
See application file for complete search history.

(56) References Cited

U.S. PATENT DOCUMENTS

| | | | | |
|---|---|---|---|---|
| 6,528,289 B1 * | 3/2003 | Fleischmann | ........ | C07K 14/285 435/252.3 |
| 2010/0034822 A1 * | 2/2010 | Masignani | ............... | A61P 31/12 424/139.1 |

OTHER PUBLICATIONS

Li, W., et al., "Recognition of conserved antigens by Th17 cells provides broad protection against pulmonary Haemophilus influenzae infection", Proc Natl Acad Sci USA. Jul. 24, 2018;115(30):E7149-E7157.
Price EP, et al., "Haemophilus influenzae: using comparative genomics to accurately identify a highly recombinogenic human pathogen", 2015, BMC Genomics 16: 641.
De Chiara M., et al., "Genome sequencing of disease and carriage isolates of nontypeable Haemophilus influenzae identifies discrete population structure", Mar. 25, 2014, Proc Natl Acad Sci USA 111(14):5439-5444.
Moffitt, K.L., et al., "TH17-Based Vaccine Design for Prevention of *Streptococcus pneumoniae* Colonization", Cell Host & Microbe, Feb. 17, 2011, 9(2):158-165.
Roier, S. et al., "Intranasal Immunization with Nontypeable Haemophilus influenzae Outer Membrane Vesicles Induces Cross-Protective Immunity in Mice", PLoS One, 2012, 7(8):e42664.
Wu, et al., "Th17-stimulating Protein Vaccines Confer Protection against Pseudomonas aeruginosa Pneumonia", American Journal of Respiratory Critical Care Medicine, 2012, 186(5):420-427.
Romero-Steiner, S. et al., Measurement of Serum Bactericidal Activity Specific for Haemophilus influenzae Type b by Using a Chromogenic and Fluorescent Metabolic Indicator Clinical and Diagnostic Laboratory Immunology, 2004 11:89-93.
Wang, Y. et al., "Cross-protective mucosal immunity mediated by memory Th17 cells against *Streptococcus pneumoniae* lung infection", Mucosal Immunology, 2017, 10:250-259.
Christensen, D. et al., "Vaccine-induced Th17 cells are established as resident memory cells in the lung and promote local IgA responses", Mucosal Immunology, 2017, 10:260-270.
Wong, S.M.S. et al., "Genome-scale approaches to identify genes essential for Haemophilus influenzae pathogenesis", Frontiers in Cellular and Infection Microbiology, Mar. 5, 2012, 2:23.
Zygmunt, B.M. et al., "Intranasal Immunization Promotes Th17 Immune Responses", Journal of Immunology, Dec. 1, 2009, 183(11):6933-6938.
LeibundGut-Landmann, S. et al., "Syk- and CARD9-dependent coupling of innate immunity to the induction of T helper cells that produce interleukin 17", Nature Immunology, 2007, 8:630-638.

* cited by examiner

*Primary Examiner* — Mary Maille Lyons
(74) *Attorney, Agent, or Firm* — Saul Ewing Arnstein & Lehr LLP; Kathryn Doyle

(57) ABSTRACT

The present invention includes methods for treating and/or immunizing against *Haemophilus influenzae*, including nontypeable *H. influenzae* (NTHi). The methods comprise administering a composition comprising *H. influenzae* proteins OppA and/or LapB.

51 Claims, 19 Drawing Sheets
Specification includes a Sequence Listing.

PCR Primers

| No. | Gene No. | Primer | Primer sequence (5'-3') |
|---|---|---|---|
| 1 | HAG00239 | Forward | GGG CCA TGG TGC AAC ACA AAC TAC TCT |
|   |          | Reverse | GGG CTC GAG TGC ATG TTT AAT AAT ATA AAG |
| 2 | HAG00264 | Forward | GGG CCA TGG TGA CAA TCC TAA CAA AAA CGA CT |
|   |          | Reverse | CGG CTC GAG CAA TCC TAA CTT TTC TTT |
| 3 | HAG01275-1 | Forward | GGC CTC GAG TGC GAT TTT CTA AAC T |
|   |            | Reverse | GGC CTC GAG CAC CCC ATA AAC AAA G |
| 4 | HAG01275-2 | Forward | GCG CCA TGG ATG GSG TGG ATT ATA T |
|   |            | Reverse | GCG CTC GAG GAA GCT ATA AAC TGC ACT |
| 5 | HAG00376 | Forward | GGG CCA TGG TGA AAA ACA TCG CAA AAG T |
|   |          | Reverse | GGG CTC GAG TTT TTT CTC TTG TGC T |
| 6 | HAG00633 | Forward | GGG CCA TGG TGA TTT TTT ACG TTG ATC AT |
|   |          | Reverse | GGG CTC GAG TGC TCG CAA AAT TGT T |
| 7 | HAG01097 | Forward | GGG CTC GAG AGT TTT ACC TTC AGC |
|   |          | Reverse | GGG CTC GAG AGT TTT ACC TTC AGC |
| 8 | HAG01360 | Forward | GGG GCG GCG GCT TTC GCA ATA CGT TTA T |
|   |          | Reverse | GCG CCA TGG TGA AAA AAC TTT TAA AAA T |
| 9 | HAG01677 | Forward | GCG CTC GAG TTT AGC TAA ACA TTC TAT G |
|   |          | Reverse | GGC CCA TGG TGA AAC ATT TTC TAC CGC CT |
| 10 | HAG00788 | Forward | CGC CCA TGG TGA ATA TCA CAG CCA T |
|    |          | Reverse | GGC CTC GAG TTT ATC CTT ATT TTG AC |
| 11 | HAG00293 | Forward | CGC CCA TGG TGA TCG TGA TCA ATT TAT |
|    |          | Reverse | GCC CTC GAG ACC TGC GCC AAA CAT AAT |

| No. | Gene No. | Primer | Primer sequence (5'-3') |
|---|---|---|---|
| 11 | HAG00293 | Forward | CGC CCA TGG TGA TCG TGA TCA ATT TAT |
|    |          | Reverse | GCC CTC GAG ACC TGC GCC AAA CAT AAT |
| 12 | HAG00342 | Forward | CCG GCT AGC ATG GCA ACC TAC TTT TCT |
|    |          | Reverse | GCG CTC GAG TTA TTT CAC TTC TTT AAA T |
| 13 | HAG00433 | Forward | CCG CCA TGG GCC AAA ATG CTA AAC GT |
|    |          | Reverse | CGC CTC GAG TTT TAA GTT TGC AAA AAC CT |
| 14 | HAG00789 | Forward | CCG CCA TGG TGC GTT GTT GTT TAG CAC T |
|    |          | Reverse | CCG CTC GAG GCC ATA AAT TGT TCC T |
| 15 | HAG00315 | Forward | CGG CCA TGG TGT CAT ACG GCA TTA AAC |
|    |          | Reverse | CCG CTC GAG GCC CAT ACG ATA GTT CGG T |
| 16 | HAG01680 | Forward | CCG CCA TGG TGC AAC AAC ACA ATC TCT |
|    |          | Reverse | CGG CCA TGG AAT TCG TCC AAA ATC AGC T |
| 17 | HAG01699 | Forward | CCC CTC GAG TTC TTC AAA ATA CCC AGC AT |
|    |          | Reverse | CGG CCA TGG TGA ATC AAA ATC TAA TTG |
| 18 | HAG00294 | Forward | GCG CTC GAG TGA AAC TTA CAT CGA AAG |
|    |          | Reverse | GGG CTC GAG TGA AAC TTA CAT CGA AAG |
| 19 | HAG00988 | Forward | GAG CTC GAG TTG ATT AAC TAA TAA AT |
|    |          | Reverse | GCG CCA TGG TGA AAA AAC ACC TTG CAG |
| 20 | HAG01892 | Forward | GCG CTC GAG GTA AAC GCG TAA ACC TAC |
|    |          | Reverse | CGG CCA TGG AAA CGT ATT CAT TAT TAC |
| 21 | HAG01363 | Forward | CGC CTC GAG CTC ACA TTG AAT TAT TAC |
|    |          | Reverse | |

FIG. 12

Th17 Cell Antigens Selected by Bioinformatic Filters.

| Protein | NT127 Locus | Rd KW20 gene ID | Known or inferred function | Size (aa) | Homology range for Hi strains[f] |
|---|---|---|---|---|---|
| 0973[a,b] | HIAG_00973 | HI0362 | iron-chelated ABC transporter periplasmic-binding protein YfeA | 393 | 96-99 |
| 1692[a] | HIAG_01692 | HI0139 | OmpP2, outer membrane protein P2 | 371 | 81-100 |
| 0956[b] | HIAG_00956 | HI0379 | iron-sulfur cluster assembly transcriptional regulator IscR | 150 | 96-99 |
| 1363[b,c] | HIAG_01363 | HI1249 | ABC transporter periplasmic component, zinc utilization protein ZevA (1) | 296 | 94-97 |
| 1677[b] | HIAG_01677 | HI0119 | Zinc ABC transporter, periplasmic-binding protein ZnuA | 347 | 88-99 |
| 0758[b] | HIAG_00758 | HI0408 | Zinc ABC transporter, ATP-binding protein ZnuC | 268 | 95-98 |
| 0789[b] | HIAG_00789 | HI0144 | NanK, N-acetylmannosamine kinase | 300 | 97-99 |
| 1690[b] | HIAG_01690 | HI0138 | RnhA, ribonuclease HI | 174 | 94-98 |
| 1680[b] | HIAG_01680 | HI0122 | MetC, cystathionine beta-lyase | 395 | 92-99 |
| 0431[b] | HIAG_00431 | HI0086 | MetB, O-succinylhomoserine (thiol)-lyase | 393 | 95-98 |
| 1315[b] | HIAG_01315 | HI0221 | GuaB, inosine-5′-monophosphate dehydrogenase | 488 | 91-99 |
| 1342[b] | HIAG_01342 | HI1277 | Mrp, ATP-binding protein, chromosome partitioning | 386 | 94-96 |
| 0293[b,d] | HIAG_00293 | HI1087 | YrbE, ABC transporter permease, membrane stability | 261 | 95-99 |
| 0176[d,e] | HIAG_00176 | HI0916 | outer membrane protein H family member Omp26 | 197 | 93-99 |
| 0630[d] | HIAG_00630 | HI1591 | outer membrane lipoprotein carrier protein LolA | 205 | 95-99 |
| 1097[c] | HIAG_01097 | HI1300 | ABC transporter ATP-binding protein uup | 213 | 92-98 |
| 1360[c] | HIAG_01360 | HI1252 | ABC transporter ATP-binding protein | 556 | 93-97 |
| 0259[a,c] | HIAG_00259 | HI1124 | oligopeptide permease ABC transporter membrane protein OppA | 541 | 98-99 |
| 0264[c] | HIAG_00264 | HI1119 | membrane protein LapB* | 292 | 97-100 |
| 1276[d] | HIAG_01276 | HI0262 | Heme-hemopexin utilization protein, HxuC | 712 | 94-95 |

[a] homologous to NTHi 86-028NP proteins identified in OMVs (2)
[b] required in NTHi/IAV coinfection (3)
[c] membrane protein (4)
[d] outer membrane protein (4, 5)
[e] homologous to OMP26 identified in (NTHi) strain 289 (6)
[f] the blast includes all the 15 completely sequenced Hi strains (Accession: CP002277.1, FQ670204.1, CP007471.1, CP000671.1, CP007472.1, CP000057.2, CP007476.1, CP007805.1, CP000672.1, L42023.1, CP005967.1, CP002276.1, FQ670178.1, CP008740.1, CP009610.1.)
* E. coli protein named LapB has been functionally characterized has no amino acid sequence similarity to LapB of NTHi

FIG. 13

PROTEIN ANTIGENS FOR VACCINATING AGAINST NONTYPEABLE *HAEMOPHILUS INFLUENZAE*

CROSS-REFERENCE TO RELATED APPLICATION

The present application is entitled to priority under 35 U.S.C. § 119(e) to U.S. Provisional Patent Application No. 62/871,433 filed Jul. 8, 2019, which is hereby incorporated by reference in its entirety herein.

STATEMENT REGARDING FEDERALLY SPONSORED RESEARCH OR DEVELOPMENT

This invention was made with government support under AI095740 and AI128569-01 awarded by the National Institutes of Health. The government has certain rights in the invention.

BACKGROUND OF THE INVENTION

The Gram-negative coccobacillus *Haemophilus influenzae* colonizes asymptomatically in the upper respiratory tract. Yet in part because of its prevalence, *H. influenzae* is also a significant cause of opportunistic disease. When host immunity is compromised, *H. influenzae* can disseminate into privileged anatomical locations and cause a wide spectrum of diseases, including otitis media, conjunctivitis, sinusitis, pneumonia, and meningitis. Some strains of *H. influenzae* express a polysaccharide capsule, which is the major target of the antibody response. Based on antibody specificity to the capsule, these strains are classified into six different serotypes (a-f). The type b serotype (Hib) is the most virulent and a significant cause of invasive diseases, such as meningitis worldwide. In addition to encapsulated strains, there is a genetically diverse group of *H. influenzae* strains that express no capsule, and are termed nontypeable *H. influenzae* (NTHi). With the introduction of highly effective conjugate vaccines against Hib and *Streptococcus pneumoniae*, NTHi has emerged as a leading cause of otitis media in children, community-acquired pneumonia (CAP), and exacerbation of chronic obstructive pulmonary disease (COPD). NTHi is identified in 20-94% of sputum and bronchoalveolar lavage samples taken from patients with CAP and is frequently found in the airways of patients with COPD. Recurring NTHi infection by a new strain is strongly associated with exacerbation in patients with COPD, leading to high rates of hospitalization and worsening of symptoms. Although antibiotic therapies are effective at reducing severity of both CAP and exacerbations of COPD, treatment failures are becoming more frequent, in large part, due to increasing resistance to the front-line (3-lactam. Moreover, frequent use of antibiotics to treat recurring infections disrupts the normal microbiome, leading to dysbiosis and accompanying disease susceptibility. Therefore, preventative strategies such as vaccination against pulmonary NTHi infection are urgently needed.

Current vaccine development effort has been focused on subunit vaccines that are targeted at eliciting antibody responses to bacterial surface proteins and lipooligosaccharide (LOS) antigens. Several surface proteins, including outer-membrane proteins (OMPs) OMP26, P6, and protein F, have been identified that elicit bactericidal antibodies and induce limited protective immunity against otitis media and pneumonia in animal models. Protein D from NTHi is included in the licensed 10-valent PhiD pneumococcal vaccine (Synflorix; GlaxoSmithKline) as the carrier protein while also serving as an immunogen for NTHi. Initial clinical trial data suggest that the Synflorix vaccine could prevent 35% of NTHi acute otitis media episodes; however, a subsequent study showed no significant protection against NTHi in otitis media nor a reduction in NTHi nasopharyngeal carriage. The limited success in the development of antibody-based NTHi vaccines has been due, in large part, to enormous sequence and structural variation of NTHi surface antigens. In addition to antigenic variation, NTHi is highly adapted to colonize the human respiratory tract and consequently has evolved numerous molecular mechanisms to evade antibody-mediated protection.

Thus, a need exists for methods of preventing and treating NTHi infections that incorporate additional antigens and engage immune mechanisms other than antibodies, and yield broad and effective protection. The present invention addresses this need.

SUMMARY OF THE INVENTION

As described herein, the present invention relates to compositions and methods for treating and/or immunizing against *Haemophilus influenzae*, including nontypeable *H. influenzae* (NTHi).

In one aspect, the disclosure provides a method of immunizing a subject against *Haemophilus influenzae*. The method comprises administering to the subject an effective amount of a composition comprising any one or both of *H. influenzae* protein OppA or *H. influenzae* protein LapB.

In another aspect, the disclosure provides a method of treating a subject at risk for developing a *H. influenzae* infection. The method comprises administering to the subject an effective amount of a composition comprising any one or both of *H. influenzae* protein OppA or *H. influenzae* protein LapB.

In another aspect, the disclosure provides a method of treating a subject, wherein the subject is infected with *H. influenza*. The method comprises administering to the subject an effective amount of a composition comprising any one or both of *H. influenzae* protein OppA or *H. influenzae* protein LapB.

In various embodiments of the above aspects or any other aspect of the invention delineated herein, administering the composition elicits a T helper 17 (Th17) response.

In certain embodiments, the OppA and/or LapB is derived from a nontypeable *H. influenzae* (NTHi) strain. In certain embodiments, the NTHi strain is NT127.

In certain embodiments, the OppA comprises the amino acid sequence of SEQ ID NO:2. In certain embodiments, the OppA is encoded by the nucleotide sequence of SEQ ID NO:1.

In certain embodiments, the LapB comprises the amino acid sequence of SEQ ID NO: 4. In certain embodiments, the LapB is encoded by the nucleotide sequence of SEQ ID NO: 3.

In certain embodiments, the subject is a human.

In certain embodiments, the composition further comprises an immunogenic adjuvant. In certain embodiments, the immunogenic adjuvant is selected from the group consisting of alum, MF59, AS03, Virosome, and AS04.

In certain embodiments, the *H. influenzae* infection is selected from the group consisting of otitis media, community-acquired pneumonia (CAP), conjunctivitis, sinusitis, meningitis, and exacerbation of chronic obstructive pulmonary disease (COPD).

In certain embodiments, the subject is at risk for *H. influenzae* due to having a comorbidity. In certain embodiments, the comorbidity is selected from the group consisting of a viral infection, a bacterial infection, a parasite, a fungal infection, and an immuno-compromised state. In certain embodiments, the viral infection is an influenza infection.

In certain embodiments, the method of treating or immunizing is cross-protective against multiple *H. influenzae* strains. In certain embodiments, the *H. influenzae* strains are selected from the group consisting of type A serotype, type B serotype, type C serotype, type D serotype, type E serotype, type F serotype, and any NTHi strain.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1A illustrates B6 mice were immunized intranasally with heat-killed NT127. Three weeks after immunization, immune mice and naive controls were challenged intranasally with different *H. influenzae* strains, or with *S. pneumoniae*. Two days after challenge, bacterial loads in the lung were determined. FIG. 1B illustrates immune sera or T cells from heat-killed NT127 immunized mice were transferred to recipient mice. Twenty-four hours later, recipient mice and naive controls were challenged intranasally with strain NT127 or RdAW. Two days after challenge, bacterial loads in the lung were determined. Each dot represents an individual mouse. Error bars=means±SEM. **P<0.0001; *P<0.001; **P<0.01; *P<0.05; NS, not significant.

FIG. 2A shows absolute numbers of CD4 and CD8 T cells from the lung and spleen of naive (open bars) and NT127-infected (black filled bars) mice. FIG. 2B illustrates CD44 expression of CD4 and CD8 T cells from the lung and spleen of naive (gray shaded) and NT127-infected (solid lines) mice. FIG. 2C illustrates production of IFN-γ and IL-17 by CD4 T cells from the lung and spleen of naive and NT127-infected mice as measured by ICS after in vitro stimulation with heat-killed NT127. FIG. 2D illustrates B6 mice were intranasally immunized with NT127. On day 7 (D7) and D21, the phenotypes of NT127-specific Th17 cells in the lung were examined and representative data were shown. n=5, error bars=means±SEM, ****P<0.0001; NS, not significant.

FIG. 3A illustrates an experimental design used herein. FIGS. 3B and 3C illustrate lung lymphocytes from NT127-infected mice (day 7) were stimulated with heat-killed bacteria, and production of IL-17 by CD4 T cells was measured by intracellular cytokine staining. In addition to different *H. influenzae* strains, *S. pneumoniae* (S.p.), *E. coli* (E.c.), *K. pneumoniae* (K.p.), and medium alone were included as controls. FIG. 3D illustrates immune sera from NT127-infected mice (3 wk) were reacted with various heat-killed bacteria as coating antigens in ELISA. Naïve sera reacting with NT127 were included as a control. FIG. 3E illustrates bactericidal activity of immune sera from NT127-infected mice against different *H. influenzae* strains. n=3-4, error bars=means±SEM, **P<0.0001; *P<0.001.

FIG. 4A illustrates an experimental design used herein. Whole-cell lysate (WCL), cytosol (Cyto), and membrane (Mem) fractions, as well as outer membrane vesicles (OMVs) were isolated from NT127, Eagan, and 86-028NP. Hi, *H. influenzae*. FIG. 4B illustrates reactivity of pooled immune sera from NT127-infected mice to different bacterial fractions analyzed by ELISA. FIG. 4C illustrates lung lymphocytes from NT127-infected mice were stimulated with different bacterial fractions, and IL-17 production by CD4 T cells was measured by ICS.

FIG. 5A illustrates purified bacterial proteins (4 and 0.4 μg) were used to stimulate pooled lung lymphocytes from NT127-infected mice, followed by ICS of IL-17. FIG. 5B illustrates pooled NT127-immune sera (1:50 and 1:400 dilutions) were reacted with purified individual proteins in ELISA. Heat-killed NT127 (NT127) and a nonrelated protein (NR) were used as a positive and negative control, respectively. FIG. 5C illustrates lung lymphocytes from mice infected with NT127, 86-028NP, Eagan, and RdAW were stimulated with purified proteins (0259, 0264, and 1360) or heat-killed bacteria (HKB) of the corresponding strains. FIG. 5D illustrates antibody responses determined on day 21 after infection. n=3, error bars=means±SEM.

FIG. 8A illustrates B6 mice were immunized with NT127 via intranasal (i.n.) or intraperitoneal (i.p.) route. On D7 after infection, NT127 specific CD4 and CD8 T cell response in the lung and spleen were examined by ICS of IFN-γ and IL-17 following stimulation with heat-killed NT127. FIG. 8B illustrates B6 WT and IL-17 KO mice were immunized i.n. or i.p. with heat-killed NT127. Three weeks after immunization, immune mice and naïve controls were challenged intranasally with the heterologous strain 86-028NP. Two days after challenge, bacterial loads in the lung were determined. n=4, error bars=means±SEM. *P<0.05; NS, not significant. L.D., limit of detection.

Figure 10B:
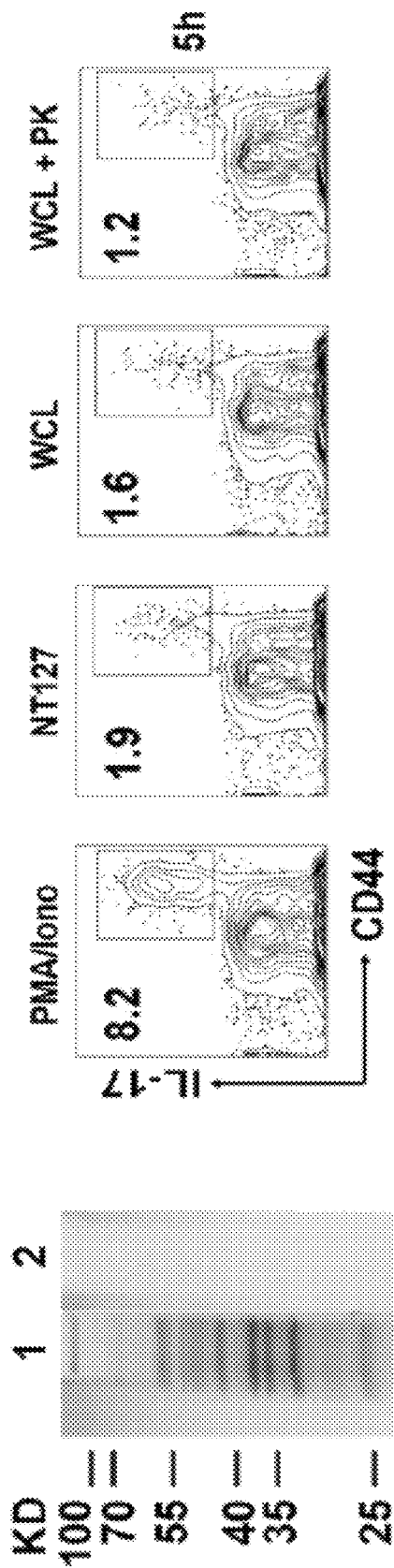
Figure 10C:
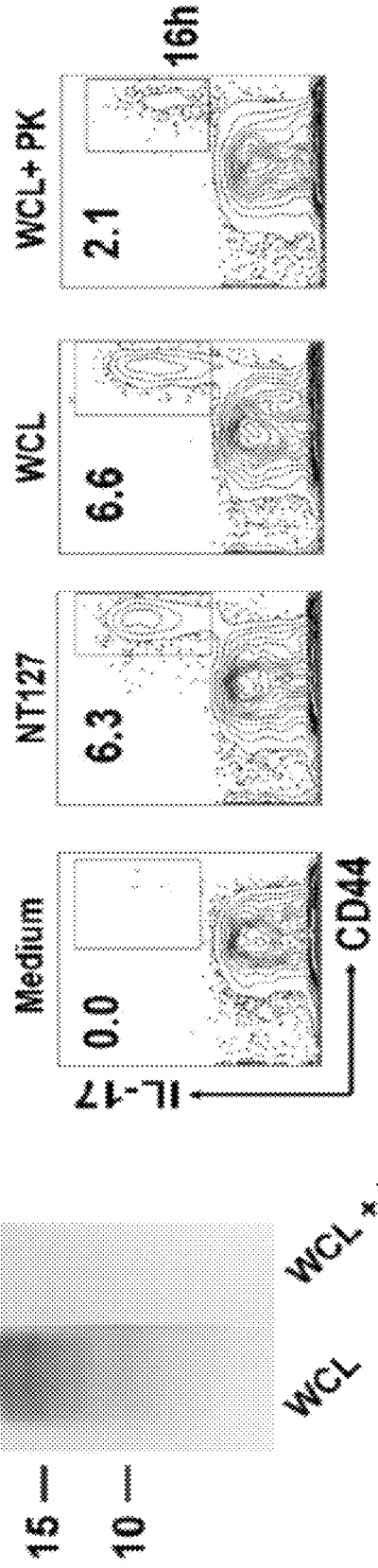
Figure 10A:
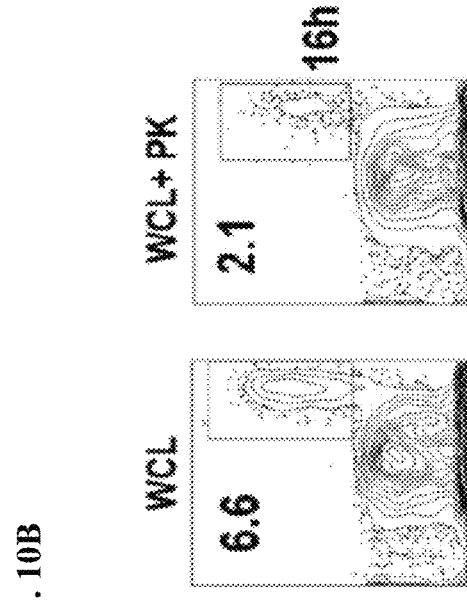

FIGS. 10A-10C are a series of graphs illustrating that the Th17 response to NTHi is directed primarily to protein antigens. FIG. 10A illustrates whole cell lysate of NT127 was treated with protease K (WCL+PK) or buffer alone (WCL) and analyzed by SDS-PAGE. FIG. 10B illustrates lung cells from NT127 infected mice were pooled and stimulated with heat-killed NT127 or NT127 cell lysate treated or untreated with protease K for 5 h. PMA/ionomycin stimulation (PMA/Iono) was used as positive control. FIG. 10C illustrates lung cells were also cultured with the indicated bacterial preparations for 16 h. Production of IL-17 by CD4 T cells was analyzed by ICS and representative data were shown.

Figure 11A:
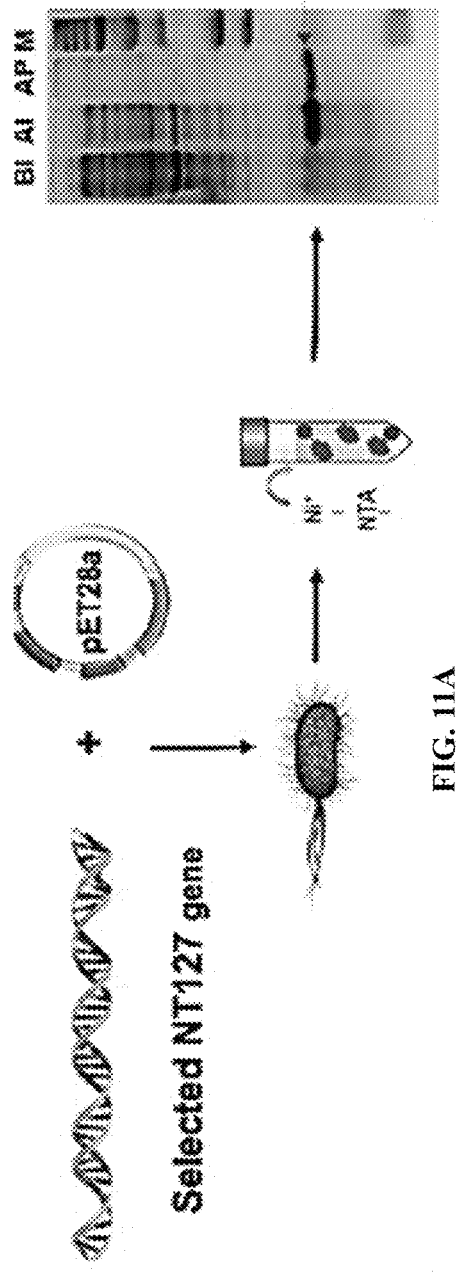
Figure 11B:
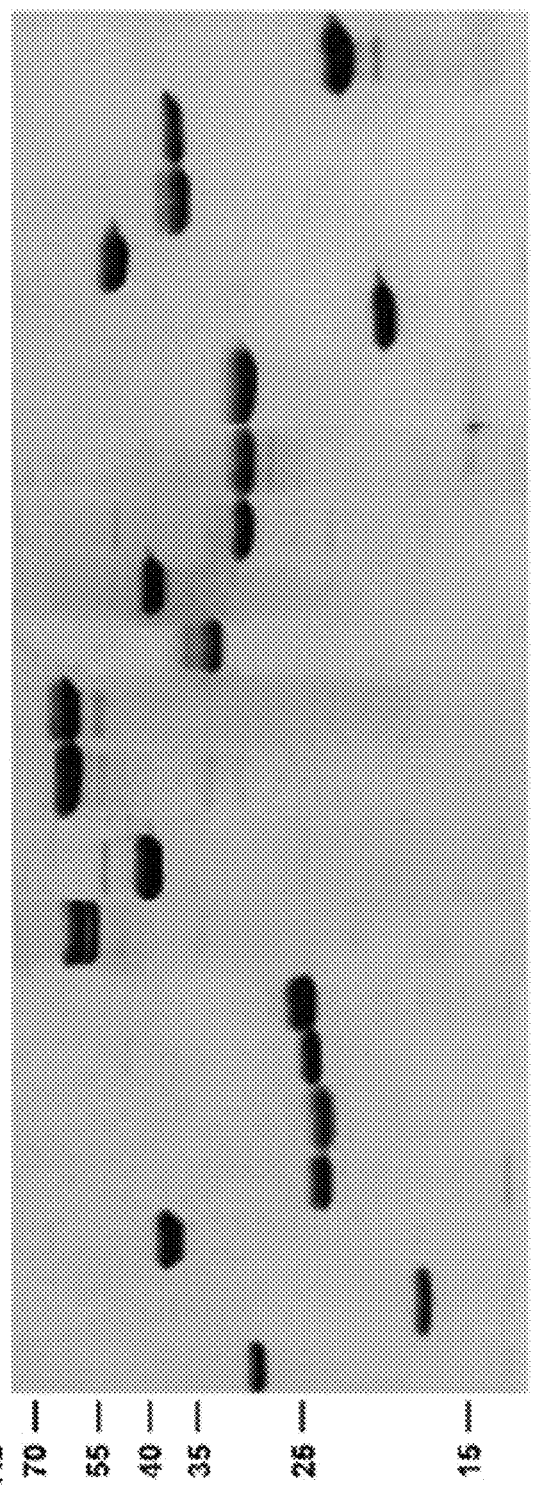
Figure 11C:
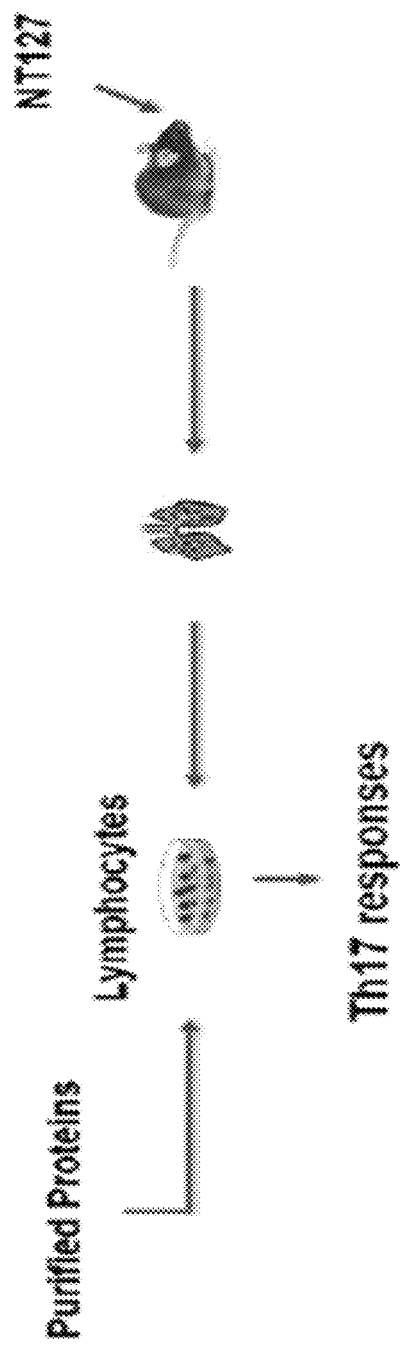
Figure 11D:
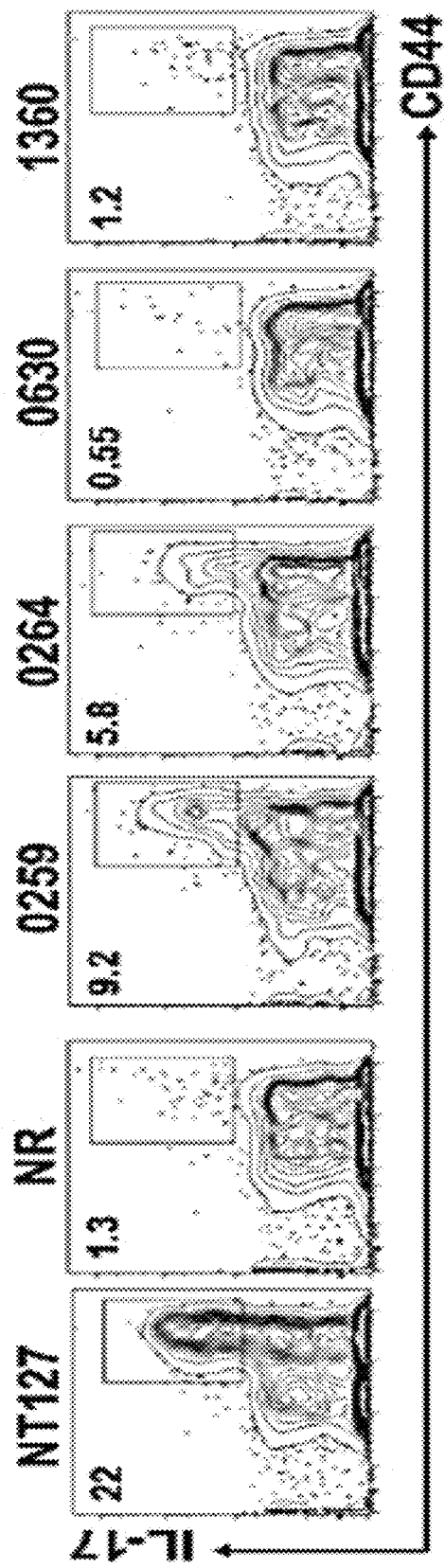

FIGS. 11A-11D are a series of graphs and images illustrating a strategy for identification of Th17 antigens. FIG. 11A is a schematic illustrating an experimental design used herein. Genes encoding selected NTHi proteins are cloned into pET28a plasmid. Recombinant proteins are expressed in *E. coli* BL21 to high levels by IPTG induction and purified by Ni affinity column. The SDS gel image shows purification of a representative protein (BI, before induction; AI, after induction; AP, after purification; M, marker). FIG. 11B depicts SDS gel images showing purity of 20 proteins purified with Ni column as described in the material and methods. FIG. 11C is a schematic illustrating an experimental design used herein. Purified individual proteins were used to simulate lung lymphocytes from NT127-infected mice, and IL-17 producing CD4 T cells were detected by ICS. FIG. 11D shows FACS plots of representative proteins that were identified as positive (0258 & 0264) and negative (0630 & 1360). Heat-killed NT127 and a non-relevant protein (NR, the negative control) were included as a positive and negative control, respectively.

FIG. 12 is a table listing DNA primers used for the amplification of the specified NTHi genes (SEQ ID NOs: 5-49). Primer sequences were designed based on the published genomic sequence of NT127 (accession no. PRJNA39125).

FIG. 13 is a table listing NTHi genes that are candidate Th17 antigens according to the bioinformatics filters used herein.

DETAILED DESCRIPTION

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule that specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies, and any modifications thereof to enhance or alter effector activity, such as glycosylation or mutations in the Fc domains (Harlow et al., 1999, In: Using Antibodies: A Laboratory Manual, Cold Spring Harbor Laboratory Press, N.Y.; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

As used herein, the term "Allogeneic" refers to any material derived from a different animal of the same species.

As used herein, the term "Xenogeneic" refers to any material derived from an animal of a different species.

The term "immunogenicity" as used herein, refers to the innate ability of an antigen or organism to elicit an immune response in an animal when the antigen or organism is administered to the animal. Thus, "enhancing the immunogenicity" refers to increasing the ability of an antigen or organism to elicit an immune response in an animal when the antigen or organism is administered to an animal. The increased ability of an antigen or organism to elicit an immune response can be measured by, among other things, a greater number of antibodies that bind to an antigen or organism, a greater diversity of antibodies to an antigen or organism, a greater number of T-cells specific for an antigen or organism, a greater cytotoxic or helper T-cell response to an antigen or organism, a greater expression of cytokines in response to an antigen, and the like.

As used herein, the terms "eliciting an immune response" or "immunizing" refer to the process of generating a B cell and/or a T cell response against a heterologous protein.

As used herein, by "combination therapy" is meant that a first agent is administered in conjunction with another agent. "In combination with" or "In conjunction with" refers to administration of one treatment modality in addition to another treatment modality. As such, "in combination with" refers to administration of one treatment modality before, during, or after delivery of the other treatment modality to the individual. Such combinations are considered to be part of a single treatment regimen or regime.

"Humoral immunity" or "humoral immune response" both refer to B-cell mediated immunity and are mediated by highly specific antibodies, produced and secreted by B-lymphocytes (B-cells).

"Adjuvant" refers to a substance that is capable of potentiating the immunogenicity of an antigen. Adjuvants can be one substance or a mixture of substances and function by acting directly on the immune system or by providing a slow release of an antigen. Examples of adjuvants are aluminium salts, polyanions, bacterial glycopeptides and slow release agents as Freund's incomplete adjuvant.

"Delivery vehicle" refers to a composition that helps to target the antigen to specific cells and to facilitate the effective recognition of an antigen by the immune system. The best-known delivery vehicles are liposomes, virosomes, microparticles including microspheres and nanospheres, polymeres, bacterial ghosts, bacterial polysaccharides, attenuated bacteria, virus like particles, attenuated viruses and ISCOMS.

The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Comorbidity" as used herein refers to the presence of one or more additional conditions co-occurring with (that is, concomitant or concurrent with) a primary condition; in the countable sense of the term, a comorbidity (plural comorbidities) is each additional condition.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "ameliorating" or "treating" means that the clinical signs and/or the symptoms associated with a disease are lessened as a result of the actions performed. The signs or symptoms to be monitored will be well known to the skilled clinician.

The term "downregulation" as used herein refers to the decrease or elimination of gene expression of one or more genes.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE, and subclasses within each class. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

When "an immunologically effective amount," "an autoimmune disease-inhibiting effective amount," or "therapeutic amount" is indicated, the precise amount of the compositions of the present invention to be administered can be determined by a physician or researcher with consideration of individual differences in age, weight, tumor size, extent of infection or metastasis, and condition of the patient (subject).

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody that recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

As used herein, the term "pharmaceutical composition" refers to a mixture of at least one compound useful within the invention with other chemical components, such as carriers, stabilizers, diluents, adjuvants, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

A "subject" or "patient," as used therein, may be a human or non-human mammal. Non-human mammals include, for example, livestock and pets, such as ovine, bovine, porcine, canine, feline and murine mammals. Preferably, the subject is human.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the unexpected discovery that administration of *H. influenzae* protein antigens OppA and LapB elicits a Th17 response that is broadly protective against infection with different serotypes and strains of *H. influenzae* including NTHi.

A growing body of evidence indicates that T cells are important in defense against respiratory infections caused by bacterial pathogens, including NTHi. Children suffering from recurring otitis media have lower cellular immune responses to the P6 protein in adenoidal lymphocytes. In adults with COPD, a lymphocyte proliferative response to P6 is associated with less severe disease exacerbations from NTHi infection. IL-17-producing CD4 T cells (Th17), first described as initiators of proinflammatory responses in autoimmune diseases, have now been shown to play an important role in several bacterial and fungal infections at mucosal sites. In murine models, it has been shown that signaling via the IL-17/IL-17R axis is important for eliminating primary lung infection by several bacterial pathogens including *Mycobacterium tuberculosis, Klebsiella pneumoniae*, and *Legionella pneumophila*. Humans with a mutation in STAT3 leading to impaired Th17 differentiation are highly susceptible to *H. influenzae* infection.

Methods of Treatment

In one aspect, the invention provides a method of immunizing a subject against *Haemophilus influenzae*, including nontypeable *H. influenzae* (NTHi), by administering to the subject an effective amount of a composition comprising *H. influenzae* protein OppA and/or *H. influenzae* protein LapB.

Another aspect of the present invention provides a method for treating a subject having a *Haemophilus influenzae* infection, including a NTHi infection, by administering to the subject an effective amount of a composition comprising *H. influenzae* protein OppA and/or *H. influenzae* protein LapB.

In another aspect the invention provides a method of treating a subject at risk for developing a *H. influenzae* infection, including a NTHi infection, by administering to the subject an effective amount of a composition comprising *H. influenzae* protein OppA and/or *H. influenzae* protein LapB.

As used herein, *H. influenzae* protein OppA refers to an oligopeptide permease ABC transporter membrane protein OppA from any *H. influenzae* strain or serotype, including nontypeable *H. influenzae* (NTHi). For example, OppA may refer to the protein encoded by locus HIAG_00259 (aka protein antigen 0259) of NTHi strain NT127 (accession no. PRJNA39125), or the protein encoded by gene HI1124 from *H. influenzae* strain Rd KW20, or any protein homologous with HIAG_00259, or any protein homologous with HI1124, or OppA from any *H. influenzae* serotype or strain including but not limited to type A serotype, type B serotype, type C serotype, type D serotype, type E serotype, type F serotype, and any NTHi. NTHi have no serotype and are a diverse collection of hundreds of different strains.

In certain embodiments, the OppA protein is derived from NTHi strain NT127. In certain embodiments, OppA comprises the amino acid sequence of SEQ ID NO: 2. In certain embodiments, the OppA comprises a protein having an amino acid sequence having 85%, 86%, 87%, 88%, 89%, 90%, 91%, 92%, 93%, 94%, 95%, 96%, 97%, 98%, or 99% sequence identity to the amino acid sequence of SEQ ID NO:2. In certain embodiments, OppA is encoded by the nucleotide sequence of SEQ ID NO: 1. In certain embodiments, the OppA comprises a protein encoded by a nucleotide sequence having 85%, 86%, 87%, 88%, 89%, 90%, 91%, 92%, 93%, 94%, 95%, 96%, 97%, 98%, or 99% sequence identity to the nucleotide sequence of SEQ ID NO: 2.

As used herein, *H. influenzae* protein LapB refers to a membrane protein LapB from any *H. influenzae* strain or serotype, including nontypeable *H. influenzae* (NTHi). For example, LapB may refer to the protein encoded by locus HIAG_00264 (aka protein antigen 0264) of NTHi strain NT127, or the protein encoded by gene HI1119 from *H influenzae* strain Rd KW20, or any protein homologous with HIAG_00264, or any protein homologous with HI1119, or LapB from any *H. influenzae* serotype including but not limited to type A serotype, type B serotype, type C serotype, type D serotype, type E serotype, type F serotype, and any NTHi.

In certain embodiments, the LapB protein is derived from NTHi strain NT127. In certain embodiments, LapB comprises the amino acid sequence of SEQ ID NO: 4. In certain embodiments, the LapB comprises a protein having an amino acid sequence having 85%, 86%, 87%, 88%, 89%, 90%, 91%, 92%, 93%, 94%, 95%, 96%, 97%, 98%, or 99% sequence identity to the amino acid sequence of SEQ ID NO: 4. In certain embodiments, the LapB is encoded by the nucleotide sequence of SEQ ID NO: 3. In certain embodiments, the LapB comprises a protein encoded by a nucleotide sequence having 85%, 86%, 87%, 88%, 89%, 90%, 91%, 92%, 93%, 94%, 95%, 96%, 97%, 98%, or 99% sequence identity to the nucleotide sequence of SEQ ID NO: 3.

In certain embodiments, when the subject is administered a composition comprising OppA and/or LapB (e.g. the is being treated or immunized), a T helper 17 (Th17) response is elicited in the subject. The OppA and LapB are bacterial antigens that are recognized by T helper 17 (Th17) cells. The Th17 response may be generated alone or in conjunction with an antibody response. The Th17 response generated by the methods disclosed herein (alone or in combination with an antibody response) is superior to an antibody response alone.

Administration of H. influenzae antigens OppA and/or LapB into a subject induces a Th17 T cell response that confers broad immunity against multiple strains of H. influenzae. Thus, cross-protection is achieved against H. influenzae strains including but not limited to type A serotype, type B serotype (e.g. Hib), type C serotype, type D serotype, type E serotype, type F serotype, and any NTHi (e.g. strains NT127, 86-028NP, PittGG, 375, 486, 2846, 2866, as exemplary strains, and any other NTHi including both genetically distinct strains and independently isolated but genetically related strains bearing different names see e.g. Price EP, et al. (2015) BMC Genomics 16: 641 and De Chiara M, et al. (2014) Proc Natl Acad Sci USA 111:5439-5444.

In certain embodiments, a subject is treated for a H. influenzae infection. A H influenzae infection is considered to be any condition, disease, disorder, or illness related to or caused by H. influenzae including but not limited to otitis media, community-acquired pneumonia (CAP), secondary post-viral bacterial pneumonia, soft-tissue infection, bone infection, bacteremia, cerebral spinal fluid infection, epiglottitis, tonsillitis, bronchitis, conjunctivitis, sinusitis, meningitis, exacerbation of Cystic Fibrosis, or exacerbation of chronic obstructive pulmonary disease (COPD).

In certain embodiments, a subject at risk for developing a H. influenzae infection is treated with the methods disclosed herein. A subject at risk for developing a H. influenzae infection may be a subject who has a pre-existing or concurrent condition, disease, disorder, or illness. Such comorbidities may include, but are not limited to, a viral infection, a bacterial infection, a parasite, a fungal infection, an immuno-compromised state as a result of infection, splenic injury, chemotherapy for other health conditions such as cancers, disruption of the microbiome by antibiotics or other causes, or genetic deficiencies in immune response components including but not exclusive to the complement system. For example, a subject may be infected with HIV or the flu (e.g. influenza virus) and would be more susceptible to H. influenzae infection. Treatment with the methods disclosed herein would offer beneficial effects to such a subject.

Compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The OppA and/or LapB may be administered concurrently, simultaneously, or separately.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, sublingual, ocular, aural, pulmonary or other mucosal administration. Intramuscular administration to the thigh or the upper arm is preferred. Injection may be via a hypodermic needle, but needle-free injection may alternatively be used.

Dosage treatment can be a single dose schedule or a multiple dose schedule. Multiple doses may be used in a primary immunization schedule and/or in a booster immunization schedule. A primary dose schedule may be followed by a booster dose schedule. Suitable timing between priming doses (e.g. between 4-16 weeks), and between priming and boosting, can be routinely determined.

Bacterial infections affect various areas of the body and so compositions may be prepared in various forms. For example, the compositions may be prepared as injectables, either as liquid solutions or suspensions. Solid forms suitable for solution in, or suspension in, liquid vehicles prior to injection can also be prepared (e.g. a lyophilized composition). The composition may be prepared for topical administration e.g. as an ointment, cream or powder. The composition be prepared for oral administration e.g. as a tablet or capsule, or as a syrup (optionally flavored). The composition may be prepared for pulmonary administration e.g. as an inhaler, using a fine powder or a spray. The composition may be prepared for nasal, aural or ocular administration e.g. as spray, drops, gel or powder e.g. (Almeida, et al. (1996) *Journal of Drug Targeting.* 3:455-467).

Antigens in the composition will typically be present at a concentration of at least 1 ug/ml each. In general, the concentration of any given antigen will be sufficient to elicit an immune response against that antigen.

Pharmaceutical Compositions

Certain embodiments of the invention are directed to prophylactically treating an individual in need thereof. As used herein, the term "prophylactic treatment" includes, but is not limited to, the administration of H. influenzae protein antigens (e.g. OppA and/or LapB) to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder.

Certain embodiments of the invention are directed to therapeutically treating an individual in need thereof. As used herein, the term "therapeutically" includes, but is not limited to, the administration of H. influenzae protein antigens to a subject who displays symptoms or signs of pathology, disease, or disorder, in which treatment is administered to the subject for the purpose of diminishing or eliminating those signs or symptoms of pathology, disease, or disorder.

Embodiments of the present invention are directed to compositions and methods for enhancing the immune response of a subject to one or more antigens (e.g. OppA and/or LapB). As used herein, the terms "subject" and "host"

are intended to include living organisms such as mammals. Examples of subjects or hosts include, but are not limited to, horses, cows, sheep, pigs, goats, dogs, cats, rabbits, guinea pigs, rats, mice, gerbils, non-human primates, humans and the like, non-mammals, including, e.g., non-mammalian vertebrates, such as birds (e.g., chickens or ducks) fish or frogs (e.g., Xenopus), and a non-mammalian invertebrates, as well as transgenic species thereof. Preferably, the subject is a human.

Compositions of the invention may include one or more pharmaceutically or physiologically acceptable carriers. A pharmaceutically acceptable carrier is a compound that does not itself induce the production of antibody or T cell responses harmful to the individual receiving the composition. Suitable carriers are typically large, slowly metabolized macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered, physiologic saline, is a typical carrier.

Compositions of the invention may include an antimicrobial, particularly if packages in a multiple-dose format.

Compositions of the invention may comprise a detergent e.g. a Tween (polysorbate), such as Tween 80. Detergents are generally present at low levels e.g. <0.1%.

Compositions of the invention may include sodium salts (e.g. sodium chloride) to give tonicity. A concentration of 10±2 mg/ml sodium chloride is typical.

Compositions of the invention will generally include a buffer. A phosphate buffer is typical.

Compositions of the invention may comprise a sugar alcohol (e.g. mannitol) or a disaccharide (e.g. sucrose or trehalose) e.g. at around 15-30 mg/ml (e.g. 25 mg/ml), particularly if they are to be lyophilized or if they include material which has been reconstituted from lyophilized material. The pH of a composition for lyophilization may be adjusted to around 6.1 prior to injection.

Compositions of the invention may include an immunogenic adjuvant. An adjuvant is a pharmacological or immunological agent that modifies the effect of other agents. Adjuvants may be added to a vaccine to boost the immune response to produce more antibodies and longer-lasting immunity, thus minimizing the dose of antigen needed. Adjuvants may also be used to enhance the efficacy of a vaccine by helping to modify the immune response to particular types of immune system cells: for example, by activating T cells instead of antibody-secreting B cells depending on the purpose of the vaccine. Immunogenic adjuvants include but are not limited to alum, MF59, AS03, Virosome, AS04, aluminum hydroxide and paraffin oil.

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulphates, etc. or mixtures of different mineral compounds, with the compounds taking any suitable form (e.g. gel, crystalline, amorphous, etc.), and with adsorption being preferred. The mineral containing compositions may also be formulated as a particle of metal salt.

Aluminum phosphates are particularly preferred, particularly in compositions which include a H. influenzae oligosaccharide antigen, and a typical adjuvant is amorphous aluminum hydroxyphosphate with PO/Al molar ratio between 0.84 and 0.92, included at 0.6 mg Al"/ml. Adsorption with a low dose of aluminum phosphate may be used e.g. between 50 and 100 ug per conjugate per dose.

Oil emulsion compositions suitable for use as adjuvants in the invention include squalene-water emulsions, such as MF59 (5% Squalene, 0.5% Tween 80, 0.5% Span 85, formulated into Submicron particles using a microfluidizer). Complete Freund's adjuvant (CFA) and incomplete Freund's adjuvant (IFA) may also be used.

Saponin compositions may also be used as adjuvants in the invention. Saponins are a heterologous group of sterol glycosides and triterpenoid glycosides that are found in the bark, leaves, stems, roots and even flowers of a wide range of plant species. Saponin from the bark of the *Ouillaia saponaria* Molina tree have been widely studied as adjuvants. Saponin can also be commercially obtained from *Smilax ornata* (sarsaprilla), *Gypsophilla paniculata* (brides Veil), and *Saponaria officianalis* (soap root). Saponin adjuvant for mulations include purified formulations, such as QS21, as well as lipid formulations, such as ISCOMs. QS21 is marketed as Stimulon™.

Additional adjuvants suitable for use in the invention include bacterial or microbial derivatives such as non-toxic derivatives of enterobacterial lipopolysaccharide (LPS), Lipid A derivatives, immunostimulatory oligonucleotides and ADP ribosylating toxins and detoxified derivatives thereof. Non-toxic derivatives of LPS include monophos phoryl lipid A (MPL) and 3-O-deacylated MPL (3dMPL). 3dMPL is a mixture of 3 de-O-acylated monophosphoryl lipid A with 4, 5 or 6 acylated chains. A "small particle" form of 3 De-O-acylated monophosphoryllipid A is also available. Such "small particles" of 3d MPL are small enough to be sterile filtered through a 0.22 um membrane. Other non-toxic LPS derivatives include monophosphoryl lipid A mimics, such as aminoalkyl glucosaminide phosphate derivatives e.g. RC-52950,51. Lipid A derivatives include derivatives of lipid A from *Escherichia coli* such as 0M-174.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAS and oligonucleotides containing palindromic or poly(dG) sequences have also been shown to be immunostimulatory. The CpG's can include nucleotide modifications/analogs such as phosphorothioate modifications and can be double-stranded or single-stranded. The CpG sequence may be directed to TLR9, such as the motif GTCGTT or TTCGTT). The CpG sequence may be specific for inducing a Th1 immune response, such as a CpG-A ODN, or it may be more specific for inducing a B cell response, such a CpG-BODN. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". Bacterial ADP-ribosylating toxins and detoxified derivatives thereof may be used as adjuvants in the invention. Preferably, the protein is derived from *E. coli* (*E. coli* heat labile enterotoxin"LT"), cholera ("CT"), or pertussis ("PT"). The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. ADP-ribosylating toxins and detoxified derivaties thereof, particularly LT-K, can be used. Numerical reference for amino acid substitutions is preferably based on the alignments of the A and B subunits of ADP-ribosylating toxins.

Proteins

The invention also provides a composition comprising *H. influenzae* protein OppA and/or *H. influenzae* protein LapB. The OppA and/or LapB proteins may comprise amino acid sequences that have sequence identity to the *H. influenzae* amino acid sequences disclosed in the examples (SEQ ID NOs: 2 and 4). Depending on the particular sequence, the degree of sequence identity is preferably greater than 50% (e.g. 60%, 70%, 75%, 80%, 85%, 90%, 91%, 92%, 93%, 94%, 95%, 96%, 97%, 98%, 99% or more). These proteins include homologs, orthologues, allelic variants and functional mutants. Typically, 50% identity or more between two polypeptide sequences is considered to be an indication of functional equivalence. Identity between polypeptides is preferably determined by the Smith-Waterman homology search algorithm as implemented in the MPSRCH program (Oxford Molecular), using an affine gap search with parameters gap open penalty–12 and gap extension penalty=1.

These proteins may, compared to the *H. influenzae* sequences of the examples (SEQ ID NOs: 2 and 4), include one or more (e.g. 1, 2, 3,4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, Substitution of single amino acids within these families does not have a major effect on the biological activity. The polypeptides may have one or more (e.g. 1, 2, 3, 4, 5, 6, 7, 8, 9, 10, etc.) single amino acid deletions relative to the *H. influenzae* sequences of the examples. The polypeptides may also include one or more (e.g. 1, 2, 3, 4, 5, 6, 7, 8, 9, 10, etc.) insertions (e.g. each of 1, 2, 3, 4 or 5 amino acids) relative to the *H. influenzae* sequences of the examples.

The invention further provides polypeptides comprising fragments of the *H. influenzae* amino acid sequences of SEQ ID NOs: 2 and/or 4. The fragments should comprise at least in consecutive amino acids from the sequences and, depending on the particular sequence, n is 7 or more (e.g. 8, 10, 12, 14, 16, 18, 20, 22, 24, 26, 28, 30, 35, 40, 45, 50, 60, 70, 80, 90, 100 or more).

The fragment may comprise at least one T-cell epitope, B-cell epitope or, preferably, a T-cell epitope that is also a B-cell epitope. T- and B-cell epitopes can be identified empirically (e.g. using PEPSCAN or similar methods) (Geysen, et al. (1984) *PNAS USA* 81:3998-4002) (Carter (1984) *Methods in Molecular Biology* 36:207-33), or they can be predicted (e.g. using the Jameson-Wolf antigenic index 5, matrix-based approaches (Raddrizzani, et al. (2000) *Briefs in Bioinformatics* 1(2):179-189), TEPITOPE (De Lalla, et al. (1999) *Journal of Immunology* 163:1725-1729), neural networks (Brrusic, et al. (1998) *Bioinformatics* 14(2):121-130), OptiMer & EpiMer (Roberts, et al. (1996) *AIDS Research and Human Retroviruses* 12(7):593-610), etc.).

Proteins of the invention can be prepared in many ways e.g. by chemical synthesis (in whole or in part), by digesting longer polypeptides using proteases, by translation from RNA, by purification from cell culture (e.g. from recombinant expression), from the organism itself (e.g. after bacterial culture, or direct from patients), etc. A preferred method for production of peptides <40 amino acids long involves in vitro chemical synthesis. (Raddrizzani, et al. (2000) *Briefs in Bioinformatics* 14(2):121-130.)(Fields, et al. (1997) *Principles of Peptide Synthesis*. ISBN: 0387564314). Solid-phase peptide synthesis is particularly preferred, such as methods based on tPoc or Fmoc chemistry (Chan, et al. (2000) *Fmoc solid phase peptide synthesis*. ISBN: 0849368413). Enzymatic synthesis may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non-natural amino acids, such as iodotyrosine or methylphenylalanine, azidohomoalanine, etc.) (Ibba (1996) *Biotechnology and Genetic Engineering Review* 13:197-216). Where D-amino acids are included, however, it is preferred to use chemical synthesis. Proteins of the invention may have covalent modifications at the C-terminus and/or N-terminus.

Proteins of the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.) Proteins of the invention are preferably provided in purified or substantially purified form i.e. substantially free from other polypeptides (e.g. free from naturally occurring polypeptides), particularly from other Haemophilus or host cell polypeptides, and are generally at least about 50% pure (by weight), and usually at least about 90% pure i.e. less than about 50%, and more preferably less than about 10% (e.g. 5%) of a composition, is made up of other expressed proteins.

Proteins of the invention may be attached to a Solid Support. Polypeptides of the invention may comprise a detectable label (e.g. a radioactive or fluorescent label, or a biotin label).

The terms "protein" and "polypeptide" refer to amino acid polymers of any length and are used interchangeably. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, Such as conjugation with a labeling component. Also included within the definition are, for example, polypeptides and proteins containing one or more analogs of an amino acid (including, for example, unnatural amino acids, etc.), as well as other modifications known in the art. Polypeptides can occur as single chains or associated chains.

Proteins of the invention can be naturally or non-naturally glycosylated (i.e. the polypeptide has a glycosylation pattern that differs from the glycosylation pattern found in the corresponding naturally occurring polypeptide).

Processes for producing proteins of the invention are known to those of skill in the art. For example, protein production may comprise the step of culturing a host cell of the invention under conditions which induce protein expression. The proteins of the invention may also be synthesized in part or in whole using chemical means.

The invention provides a composition comprising one or more polypeptides of the invention.

Various tests can be used to assess the in vivo immunogenicity of proteins of the invention. For example, polypeptides can be expressed recombinantly and used to screen patient sera by immunoblot. A positive reaction between the polypeptide and patient serum indicates that the patient has previously mounted an immune response, specifically an antibody response, to the protein in question i.e. the protein is an immunogen. This method can also be used to identify immunodominant proteins. T cell assays using PBMC can be screened with polypeptides or proteins of the invention. For example, PBMC can be stimulated with proteins or polypeptides of the invention and assessed for T cell activation and cytokine production. A positive response, especially by Th17 cells indicates the immunogenicity of the proteins of the invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

EXPERIMENTAL EXAMPLES

The invention is now described with reference to the following Examples. These

Examples are provided for the purpose of illustration only, and the invention is not limited to these Examples, but rather encompasses all variations that are evident as a result of the teachings provided herein.

The materials and methods employed in these experiments are now described.

Mice. Specific pathogen-free, 6- to 8-wk-old C57BL/6 mice were purchased from the National Cancer Institute. IL-17A-deficient (IL-17 KO) mice were bred in house at the University of Pennsylvania. All experiments were performed in accordance with Institutional Animal Care and Use Committee-approved protocols in the University of Pennsylvania animal facility.

Bacteria Strains and Growth Conditions. NTHi strains were cultured in brain heart infusion (BHI) broth supplemented with 2.0% (vol/vol) Fildes enrichment (BD) and 10 µg/mL NAD (Sigma) (sBHI) or on sBHI agar plates at 37° C. For preparation of nonviable NTHi, bacterial suspension was heated to 65° C. for 30 min and plated to ensure 100% bacterial killing.

Expression and Purification of Recombinant NTHi Proteins from $E.\ coli$. The His-tagged proteins were expressed and purified as described (Moffitt, et al. Cell Host & Microbe, 2011, 9:158-165) with slight modifications. Briefly, DNA sequences encoding the selected NTHi proteins were amplified by PCR using primers (FIG. 12) designed based on the published genomic sequence of NT127 (accession no. PRJNA39125). Purified PCR products were cloned into the pET28a expression vectors, and the fusion constructs were confirmed by DNA sequencing. $E.\ coli$-containing expression vectors were grown in 200 mL LB broth in the presence of 0.1 mM IPTG and cultured for 4 h at 30° C. Proteins were purified over Ni columns. Inclusion bodies, when present, were solubilized with 8 M urea before being loaded onto Ni columns. The resulting proteins were analyzed by SDS/PAGE with Coomassie staining to confirm purity.

Fractionation of $H.\ influenzae$ Proteins and Immunoblot Analysis. Fractionated proteins were prepared according to the protocol of Roier et al. (Roier, et al. PLoS One, 2012, 7:e42664). Briefly, bacteria were harvested from overnight cultures and washed with PBS. Cells were then resuspended in PBS with protease inhibitor and disrupted by sonification. After removal of unbroken cells, the whole-cell lysates were separated into cytoplasmic (supernatant) and membrane (pellet) fractions by ultracentrifugation. The membrane pellet was washed three times and resuspended in PBS. OMVs were harvested from supernatants of overnight culture by filtration and ultracentrifugation and then resuspended in PBS. All fractions were stored at −20° C. before use.

Animal Immunization and Infection. For whole-cell antigen (WCA) immunization, mice were anesthetized by i.p. injection of 100 µL ketamine/xylazine (100 mg/3.8 mg/kg) and inoculated with $1 \times 10^8$ heat-killed NT127 in 30 µL PBS (i.n.). For immunization with proteins, mice were immunized i.n. three times, at weekly intervals, with 40 µL PBS containing 5 µg of each NTHi protein (0.125 mg/mL) plus the adjuvant curdlan (5 mg/mL) (Sigma-Aldrich) (Wu, et al. *American Journal of Respiratory Critical Care Medicine,* 2012, 186:420-427). On day 21 after the final immunization, while anesthetized, mice were challenged i.n. with 30 µL of PBS containing ~$10^8$ cfu of the indicated $H.\ influenzae$ strain. Forty-eight hours after challenge, the number of $H.\ influenzae$ in lung homogenates was determined.

Serum Bactericidal Assay. The sensitivity of heterologous $H.\ influenzae$ strains to anti-NT127 serum was determined as previously described, using mouse naive or anti-NT127 immune sera and complement from infant rabbit (Romero-Steiner, et al. *Clinical and Diagnostic Laboratory Immunology,* 2004 11:89-93). Mouse naive and anti-NT127 immune sera were heat inactivated by incubating at 56° C. for 30 min. Results were reported as percent survival (calculated by dividing total colony-forming units of immune serum-treated samples by total colony-forming unit counts of samples treated with naive serum).

IgG Measurement by ELISA. Diluted heat-killed bacteria (~$3 \times 10^8$ cfu), cellular fraction (1 mg/mL in PBS), or purified proteins (1 mg/mL in PBS) were coated onto 96-well plates by incubation at 37° C. for 1 h. Wells were then blocked with 2% nonfat milk in PBS. Twofold serial dilutions of pooled mouse sera were applied to the wells in duplicate at appropriate dilutions. Plates were incubated with sera for 1 h at 37° C. Antibodies were detected with goat anti-mouse IgG-HRP (H+L). For detection, the 3,3',5,5'-tetramethylbenzidine (TMB)peroxidase substrate reagent set (BioLegend) was used according to the manufacturer's instructions. Optical densities were read at 450 nm with a microplate reader.

Intracellular Cytokine Staining and Flow Cytometry. Lung and spleen cells were isolated and stimulated with heat-killed *H. influenzae* strains for 16 h at 37° C. with Golgi block added for the last 5 h. Cells were then stained as described in our previous study (Wang, et al. *Mucosal Immunology*, 2017, 10:250-259). All samples were analyzed with FACSCanto. FACS data were analyzed with FlowJo software.

Adoptive Transfer Experiments. For serum transfer, each naive mouse was injected i.v. with 200 μL sera from immunized mice. Total T cells and CD4 T cells were purified from the lung and spleen cell preparations by using MACS Pan T Cell Isolation Kit II or CD4 microbeads (Miltenyi Biotec). Approximately $5\times10^6$ cells were adoptively transferred into naive recipients via the i.v. route. Mice were then infected with *H. influenzae* 24 h following sera or T-cell transfer. Two days after infection, bacteria from lung homogenates were enumerated as described above.

In Vivo Staining with Anti-CD45.2. Anti-mouse CD45.2-FITC (clone 104; BD Biosciences) was diluted to 10 μg/mL in sterile PBS and 250 μL of the solution was injected i.v. via the tail vein 3 min before killing and sample harvest as described by Christensen et al. (Christensen, et al. *Mucosal Immunology*, 2017, 10:260-270).

Statistical Analysis. All analyses were performed using Prism software (GraphPad Software). Unpaired, one-tailed, Student's t tests were used to calculate statistical significance between two groups. The colony-forming unit data that fell below the limit of detection were assigned a value below that limit. The Kruskal-Wallis test was used to evaluate variance among all groups. If a significant variance was found, the Mann-Whitney test was used to identify significant differences between individual groups.

```
Haemophilus influenzae HIAG_00259 oligopeptide
permease ABC transporter membrane protein OppA
nucleic acid sequence
                                        (SEQ ID NO: 1)
ATGCAACACAAACTACTCTTCTCTGCAATCGCTCTTGCCCTTTCCTATTC

TGCGCAAGCAGTTATAGTGCCTGAAGGAACACAATTAGATGAAAACAAC

ATATCGTCATCAATAACGGGGCTGAACCGCAAAGTTTTGACCCACACAAA

ACCGAAGGTGTGCCAGAATCTAACGTTGCTTATCAATTACTTGAAGGCTT

AGTCACCTCAGACTCTGAAGGTAAACTTCAACCGGGTGCGGCTGAAAGCT

GGGAAAATACACCTGACTTCAAAACCTGGACATTCCATTTACGTAAAGAT

GCTAAATGGTCAAACGGAGATCCTGTTACTGCACACGATTTCGTGTTTGC

GTGGCGTCGTTTAGTGGATCCTGCAACTGCTGCACCTTACGCGAGTTACC

TAAGTTATTTACAAGTTGAAAATGCACAAGACATTATTGACGGTAAGAAA

AAACCGGCTGAATTAGGCGTGGAACAAAAGATGATTACACCTTTGTGGTT

CATACAACCAATCCTGTGCCTTATACAGTCAGTTTCGACTCACCAATCCT

TATTGCCATTACCANAAAAAGTAGTCGAAAAATTGGGTGATGCATGGGTG

AAAAAAGAAACTACGTGGGTAACGGTGCGTATAAGCTGGCTAACCACAT

CATTAACGAAAAAATCGAATTTGAACGTAACCCACTTTATTGGAACGATA

AAGAAACCGTAATCAATAGCGCGACATTCCTCGCCATTGAAAACCCAAGT

ACCGATGTAGCGCGTTATCGTGCGGGCGATTTAGACATGACCAGTTATGG

TTTACCGCCAGAACAATTCGCTAAATTACAAAAAGAATTGCCAGGCGAAG

TATACGTTACTCGTACCCTAGGAACTTATTCTTATGAATTAAACAATAAG

AAAGCACCTTTTGATAACGTGAATATTCGTAAAGCCTTGAACTTATCCCT

TGATCGTAATGTGATCACCGATAAAGTATTGGGTCAAGGTCAAACACCAA

CCTATGTGTTTACCCCAACTTACATCGAAGAAGGTCATCTCATTCAACAA

CCTGCTTATTCAAAAGAACCGATGGCACAACGTAATGAAGAAGCCATTAA

ACTCTTAGAAGAAGCTGGTTACAGTAAAGCGAATCCGTTGAAATTCAGCA

TTCTTTATAATACCAATGAAAACCACAAAAAAGTGGCTATTGCTGCAGCA

TCTATGTGGAAAGCTAACACCAAAGGTTTGATTGACGTGAAATTAGAAAA

CCAAGAGTGGAAAACTTACATTGATAGCCGTCGTGCAGGTCGTTACGATG

TGGCGCGTGCTGGATGGAATGCGGATTACAACCAAGCAACAACATTCGGC

AACTATTTCTTATCTAATTCTAGTAACAATACCGCGAAATATGCGAATCC

AGAATATGATAAAGCGATGGCAGAATCTTACGCAGCAACGGATGCAGAAG

GTCGTGCAAAAGCTTATGCGAAAGCCGAAGAAATTCTTGGAAAAGATTAC

GGTATCGTACCAATCTTTAACTATGTGAATCCACGCTTAGTGAAACCTTA

CGTAAAGGTTATTCAGGCAAAGATCCACAAGATCATATTTACTTACGCA

ATCTTTATATTATTAAACATTAA

Haemophilus Influenzae HIAG_00259 oligopeptide
permease ABC transporter membrane protein OppA
amino acid sequence
                                        (SEQ ID NO: 2)
MQHKLLFSAIALALSYSAQAVIVPEGTQLDEKQHIVINNGAEPQSFDPHK

TEGVPESNVAYQLLEGLVTSDSEGKLQPGAAESWENTPDFKTWTFHLRKD

AKWSNGDPVTAHDFVFAWRRLVDPATAAPYASYLSYLQVENAQDIIDGKK

KPAELGVEKDDYTFVVHTTNPVPYTVSTHQSLLPLPKVVEKLGDAWVKKE

NYVGNGAYKLANHIINEKIEFERNPLYWNDKETVINSATFLAIENPSTDV

ARYRAGDLDMTSYGLPPEQFAKLQKELPGEVYVTRTLGTYSYELNNKKAP

FDNVNIRKALNLSLDRNVITDKVLGQGQTPTYVFTPTYIEEGHLIQQPAY

SKEPMAQRNEEAIKLLEEAGYSKANPLKFSILYNTNENHKKVAIAAASMW

KANTKGLIDVKLENQEWKTYIDSRRAGRYDVARAGWNADYNQATTFGNYF

LSNSSNNTAKYANPEYDKAMAESYAATDAEGRAKAYAKAEEILGKDYGIV

PIFNWNPRLVKPYVKGYSGKDPQDHIYLRNLYIIKH

Haemophilus influenzae HIAG_00264 membrane protein
LapB nucleic acid sequence
                                        (SEQ ID NO: 3)
ATGGCAATCCAGATGACAACAAAAACAACTTACCAATGGCCTCAATCTAA

GGATATTTATCCATATCGACCAGGGCGTTTTGATGCACCAAAACATTGGC

GTTATAACTTACGTAGCTTTTTAAATCGTGGTTCAATTCGTCGCTTTGAA

CAATTTATCAATCAGCATCCTTTTCTCATCGATATTTTTAATACGCACTT

GGATTATAGTTATCCTGTTGCTTGTCGTTTTTTAGATAAGCGTTTTAACG

CATCACAGCGTTTTCATGCGGTTTGTGAGAATCTTTTATTTTTACCCGAA

AAACTTACCGCACTTTCTACGCCGTTATGGGAAAAACCTCTAAGTTTTGG

CGAAGTCATTCCTGATTTTGAAATGACATTAAGCATGACAACCCATCAAC

CGATGGAAGGATATTGGGTATTGGAGCTATGGCATAAACCAAGAAACGAA
```

-continued

```
TTAGTCTATTTGCTTACTTTTGCCAAATTGGGCGATGCGTTGCTTATTGC

TGTTGTACAAGGGCCAAATTTTGAAGGCTCAAAGGAAATGGTGAAACAAC

TAACCAAATTATGCCACGGTTTACGCCCTGCCTATTTAATGGTTGAAACC

ATGAAATCACTCACAAAAATACTAGGCTACAATAAATTGCTGGGCATTCC

ACAAAAATACCAAAATAAATCTCGTTTCATCCAAAGCAAACAATATACAG

TGGACTATGATGCAATTTTTGGCGAATCAGGCGGAGAATTAAAAGATTAC

TGGGAATTGCCTTTAGAAATGGATAGAAATCTAGATGATATTCCAAGTAA

AAAACGTTCCATGTATCGTAAGCGTTATGCGATGCTAGATGATTTGGCTA

AGGTAATTGAAGAAAAGTTAGGATTGTAA
```

Haemophilus influenzae HIAG_00264 membrane protein
LapB amino acid sequence
(SEQ ID NO: 4)

```
MAIQMTTKTTYQWPQSKDIYPYRPGRFDAPKHWRYNLRSFLNRGSIRRFE

QFINQHPFLIDIFNTHLDYSYPVACRFLDKRFNASQRFHAVCENLLFLPE

KLTALSTPLWEKPLSFGEVIPDFEMTLSMTTHQPMEGYWVLELWHKPRNE

LVYLLTFAKLGDALLIAVVQGPNFEGSKEMVKQLTKLCHGLRPAYLMVET

MKSLTKILGYNKLLGIPQKYQNKSRFIQSKQYTVDYDAIFGESGGELKDY

WELPLEMDRNLDDIPSKKRSMYRKRYAMLDDLAKVIEEKLGL
```

The results of the experiments are now described.

Example 1: Protection Against Homologous and Heterologous Strains by Immunization with Heat-Killed Bacteria.

Figure 1A:
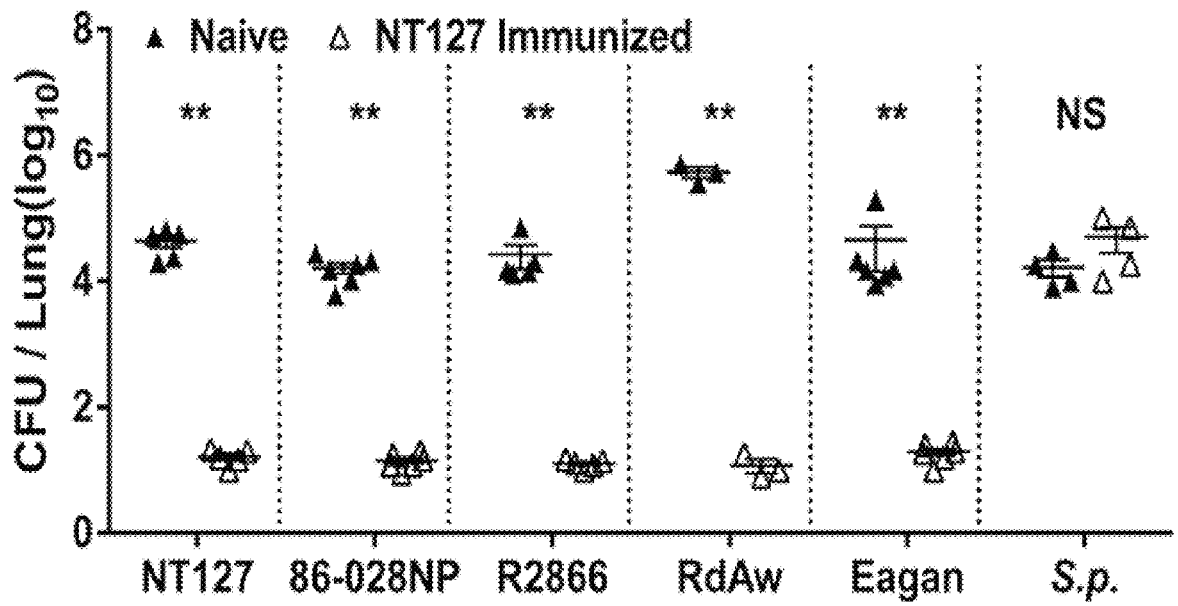
FIGS. 1A-1B are a series of graphs demonstrating that vaccination induces broad protective immunity against lung infection by different strains of NTHi.
Figure 1B:
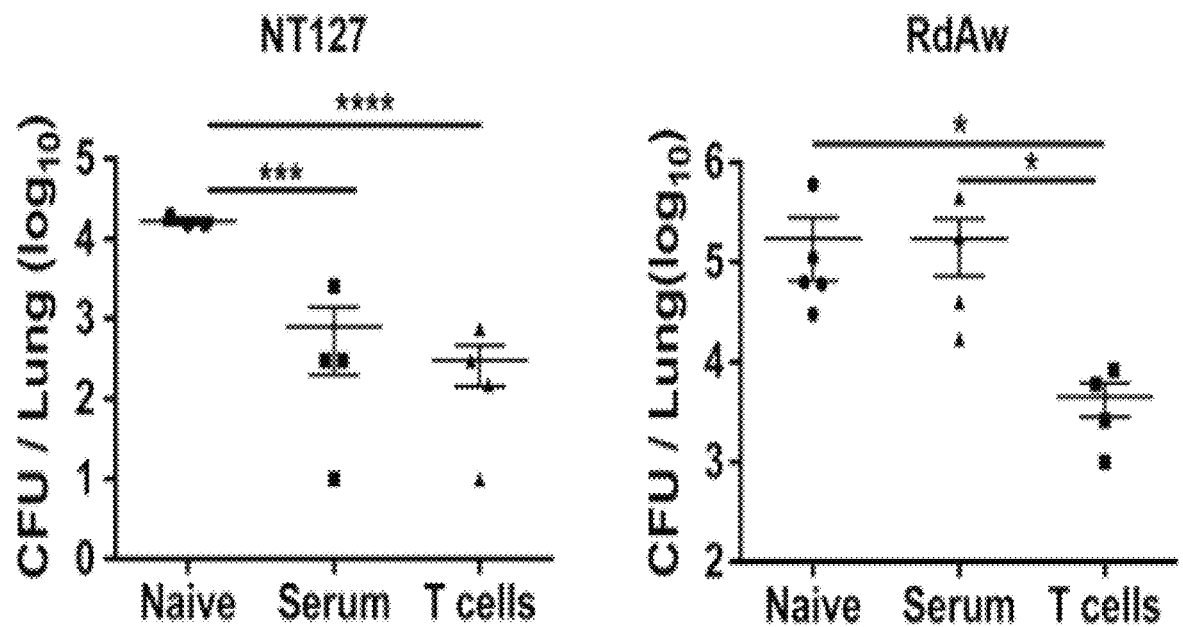

To test whether broad protection against NTHi lung infection can be induced, C57BL/6 mice were immunized intranasally with heat-killed NT127, a clinical NTHi isolate that has been well characterized genetically and in the murine model of lung infection. Three weeks later, mice were challenged with the homologous NT127 or heterologous strains by the intranasal route under anesthesia, which results in direct infection of the lower respiratory tract and acute bacterial pneumonia. Immunized animals had ~1,000-fold lower bacterial burdens in the lung on day 2 post challenge (FIG. 1A), compared with the unimmunized controls. This protection was observed not only in mice challenged with the homologous NT127 strain, but also after heterologous challenge with NTHi strains 86-028NP and R2866, and even strains of encapsulated lineages, Eagan (serotype b) and RdAW (serotype d derived). However, the NT127-immunized mice were not protected from challenge with S. pneumoniae, another common respiratory bacterial pathogen (FIG. 1A). Together, these results show that immunization with heat-killed NT127 induced H. influenzae-specific immunity that was broadly protective against pulmonary infection by different H. influenzae strains. The role of immune antibodies and T cells in mediating the homologous and heterologous protection was then investigated. Sera and purified T cells from NT127-immunized mice were adoptively transferred into naïve mice, which were then challenged with NT127 or RdAW. Both sera and T cells conferred comparable protection against homologous challenge with NT127. In contrast, only T-cell recipient mice were protected from heterologous RdAW challenge (FIG. 1B). These data indicate that T cells play a predominant role in mediating heterologous protection in pulmonary H. influenzae infection.

Example 2: A Robust Th17 Response in the Lung and its Role in Heterologous Protection.

Figures 2A, 2B:
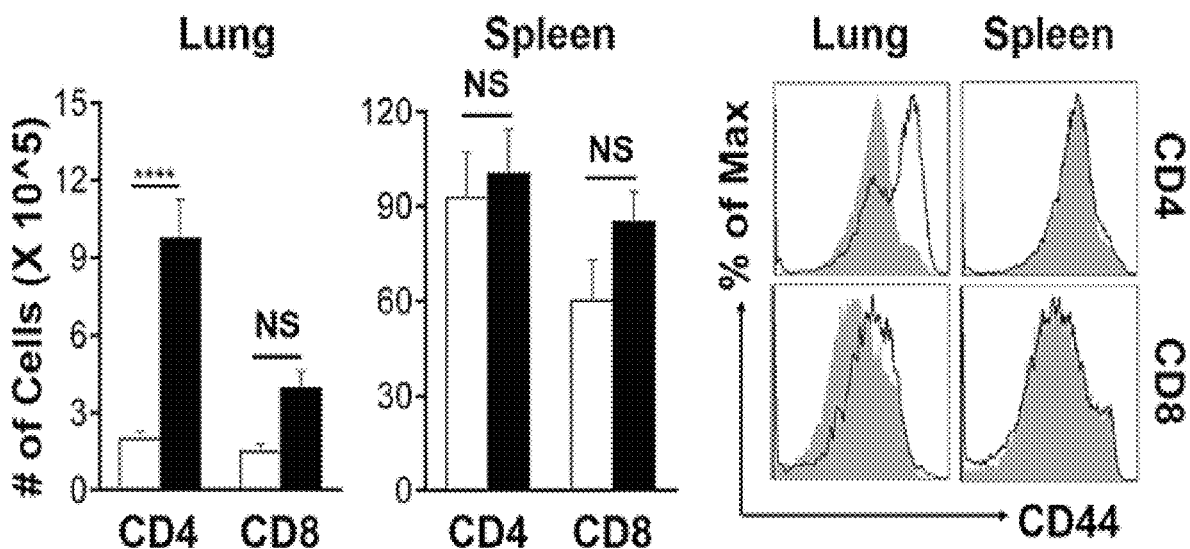
FIGS. 2A-2D are a series of graphs that illustrate NTHi infection induces a robust Th17 response in the lung. B6 mice were intranasally infected with NT127. On day 7, lymphocytes from the lung and spleen were isolated for analyses.
Figure 2C:
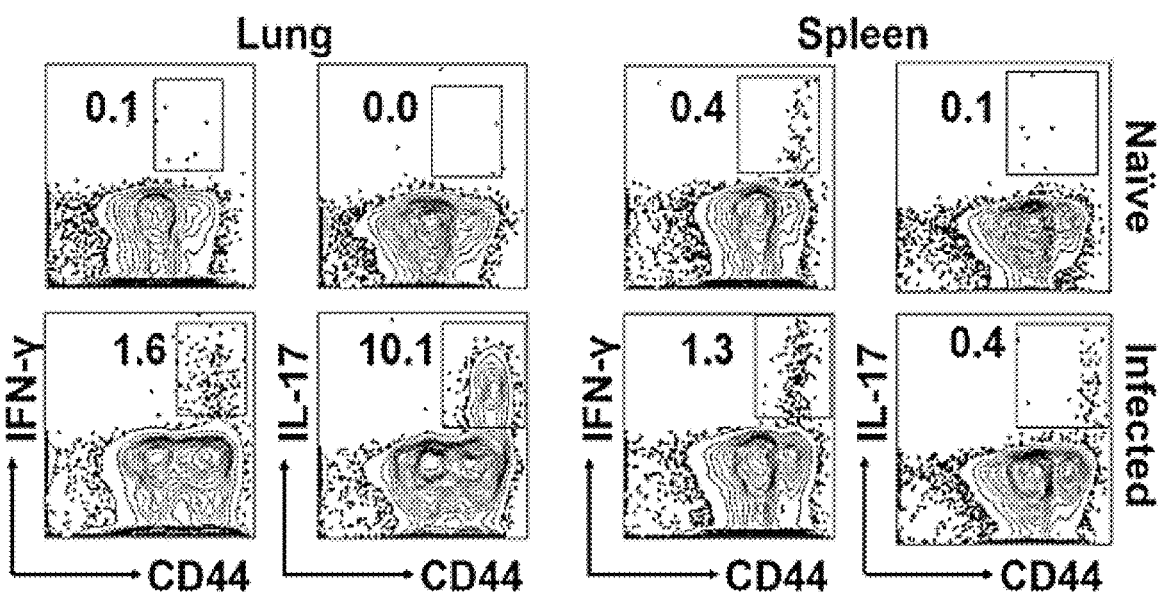
Figure 6B:
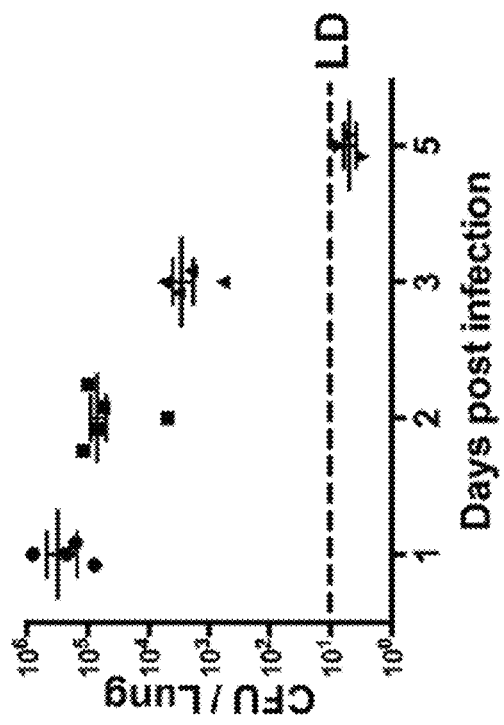
FIGS. 6A-6D are a series of graphs showing the kinetics of immune response to NT127 infection. B6 mice were infected with NT127. Body weight change (FIG. 6A) and bacteria load in the lung (FIG. 6B) were measured. Kinetics of NT127-specific CD4 T cells producing IFN-γ (Th1) and IL-17 (Th17) (FIG. 6C), and antibody responses (FIG. 6D) were determined. n=3-4, error bars=means±SEM. * P<0.001; P<0.01; * P<0.05. LD, limit of detection.
Figure 6D:
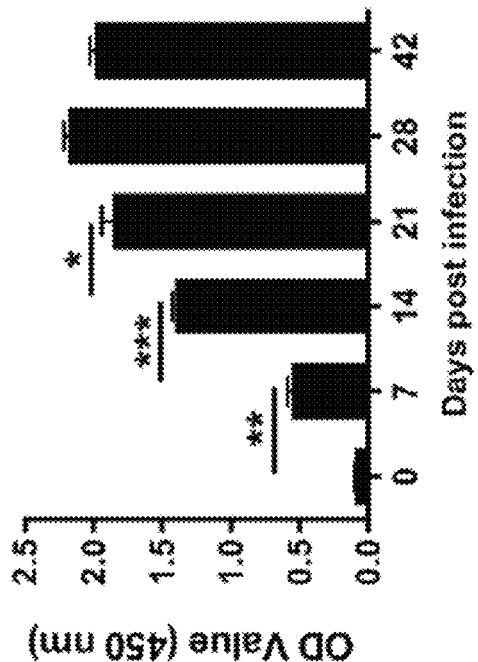
Figure 6A:
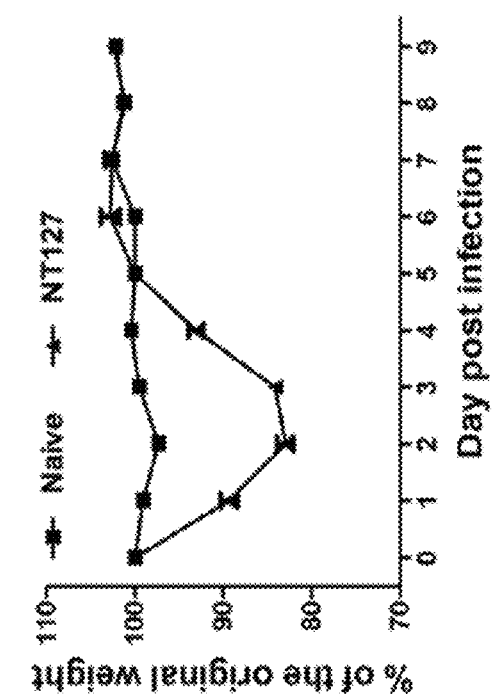
Figure 6C:
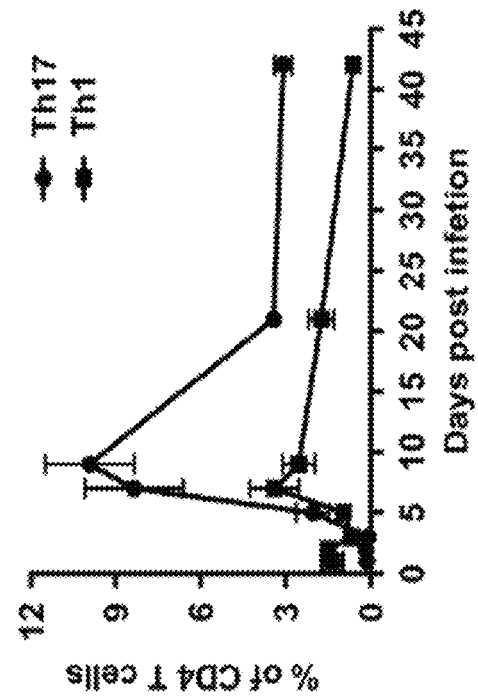
Figure 7A:
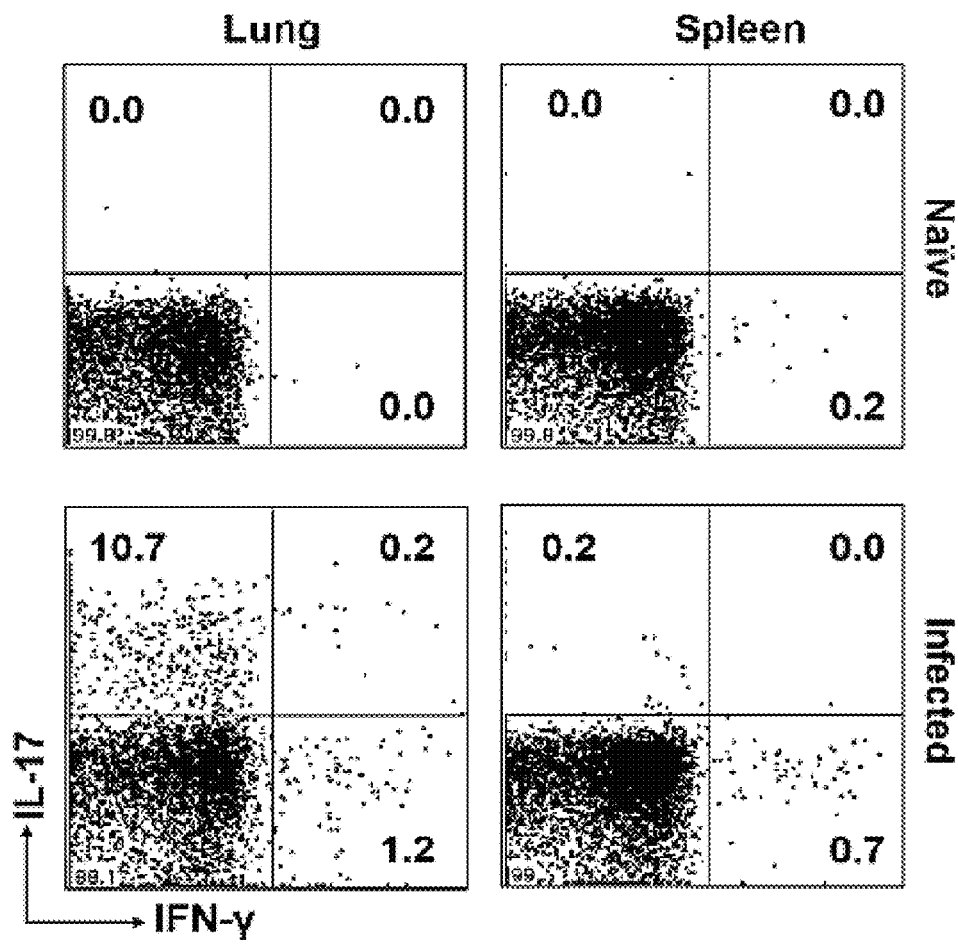
FIGS. 7A-7B are a series of plots depicting production of cytokines by T cells after NT127 infection. Lymphocytes from the lung and spleen of NT127-infected mice (day7) were stimulated with heat-killed NT127, followed by ICS for IFN-γ/IL-17 co-expression by CD4 T cells (FIG. 7A), and production of IFN-γ and IL-17 by CD8 T cells (FIG. 7B).
Figure 7B:
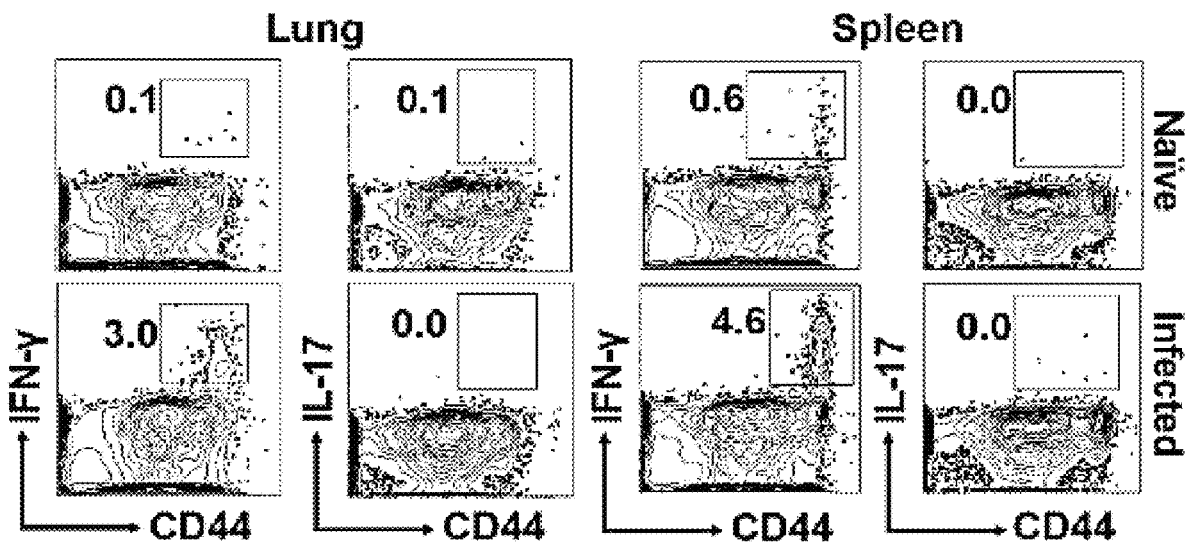

Since T cells were capable of mediating heterologous protection, the T-cell response to pulmonary NTHi infection was characterized. Mice were infected with a sub lethal dose of NT127, and the body weight, bacterial loads, NT127-specific antibody, and T-cell responses were analyzed on different days after infection (FIG. 6). By day 7 when the NT127-specific T-cell response reached the maximum, there were substantial increases in the percentage and number of total CD4 but not CD8 T cells in the lungs of infected mice compared with naïve controls. The majority of CD4 T cells in the lungs of infected mice had an activated CD44hi phenotype. In the spleen, there were no differences in either the quantities or CD44 expression levels of CD4 and CD8 T cells between infected and naïve mice (FIGS. 2A and 2B). Thus, NT127 infection induced a strong CD4 but not CD8 T-cell response that was localized in the lung. To study the functions of responding T cells, lymphocytes from lung and spleen (day 7 after NT127 infection) were stimulated with heat-killed NT127 followed by intracellular cytokine staining (ICS). A small percentage (~1.6%) of CD4 T cells from the lungs of immunized mice produced IFN-γ, while a high percentage of them (>10%) produced IL-17 (FIG. 2C). A small percentage of CD4 T cells in the spleens of immunized mice produced IFN-γ (1.3%) or IL-17 (0.4%). All cytokine-producing CD4 T cells had an activated CD44hi phenotype and produced either IL-17 or IFN-γ; very few of them, if any, were IL-17/IFN-γ coproducers (FIG. 7A). CD4 T cells from the lungs or spleens of naïve mice produced little IFN-γ or IL-17 when stimulated in vitro with heat-killed bacteria. Unlike CD4 T cells, CD8 T cells from both lung and spleen produced only IFN-γ (3% and 4.6%, respectively) and little IL-17 (FIG. 7B).

Figure 2D:
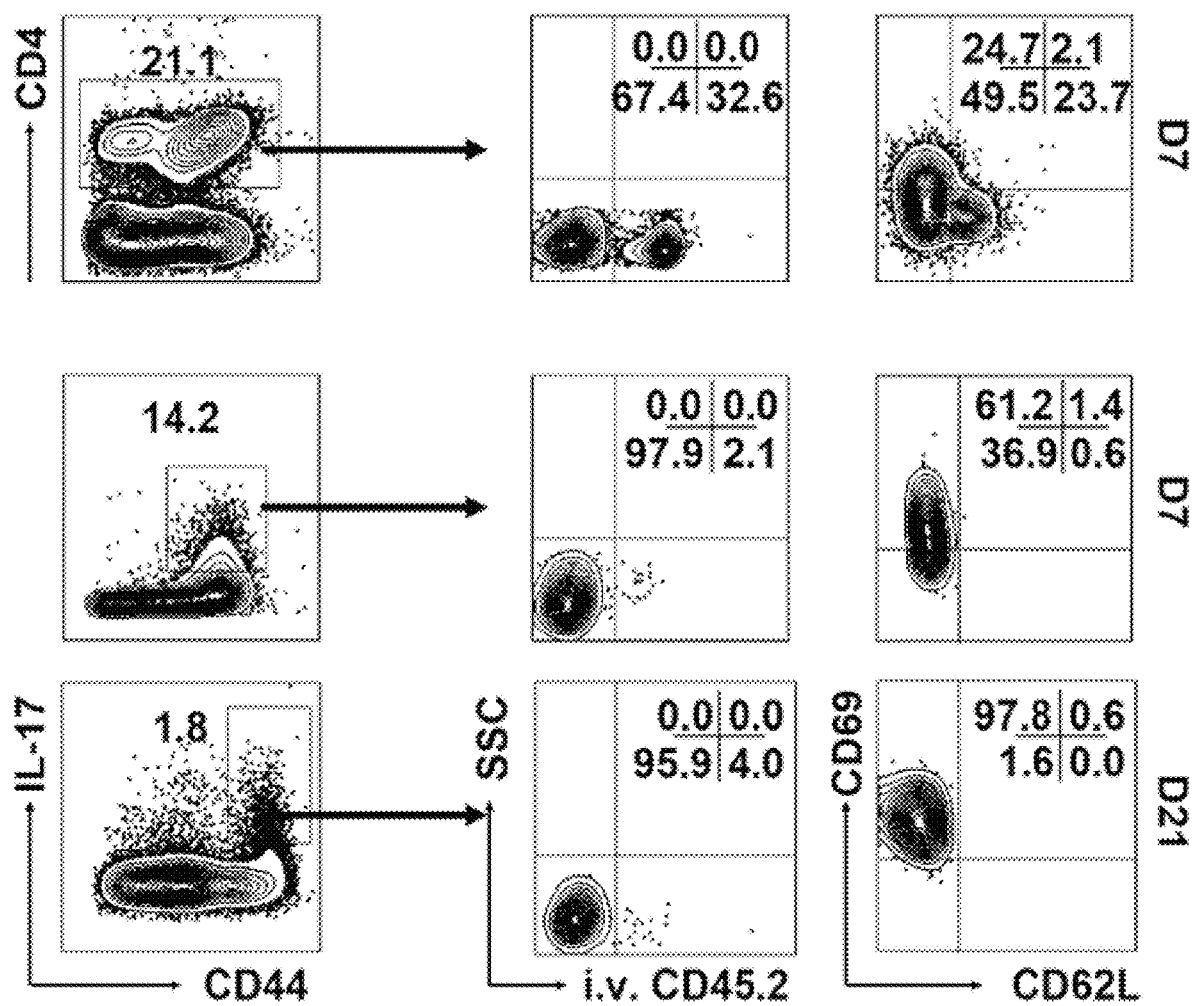
Figure 8A:
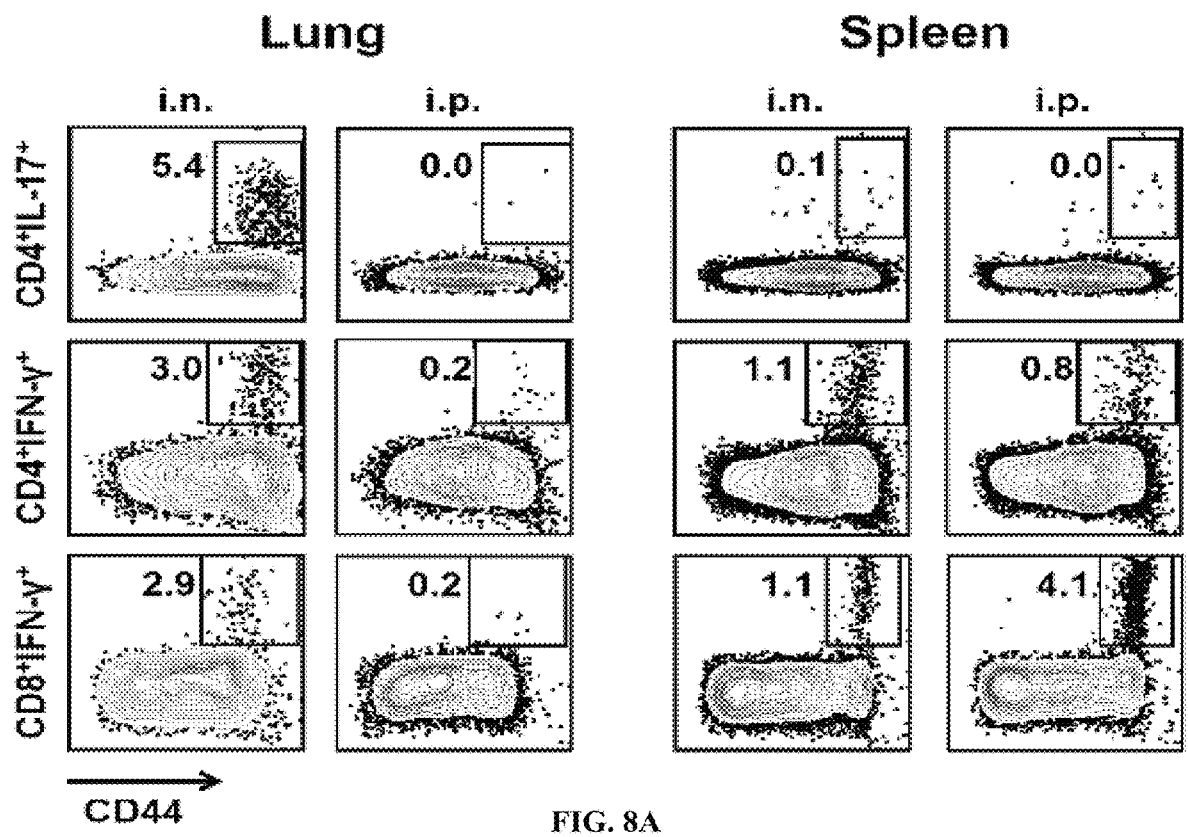
FIGS. 8A-8B are a series of plots illustrating that IL-17 is important for heterologous protection.
Figure 8B:
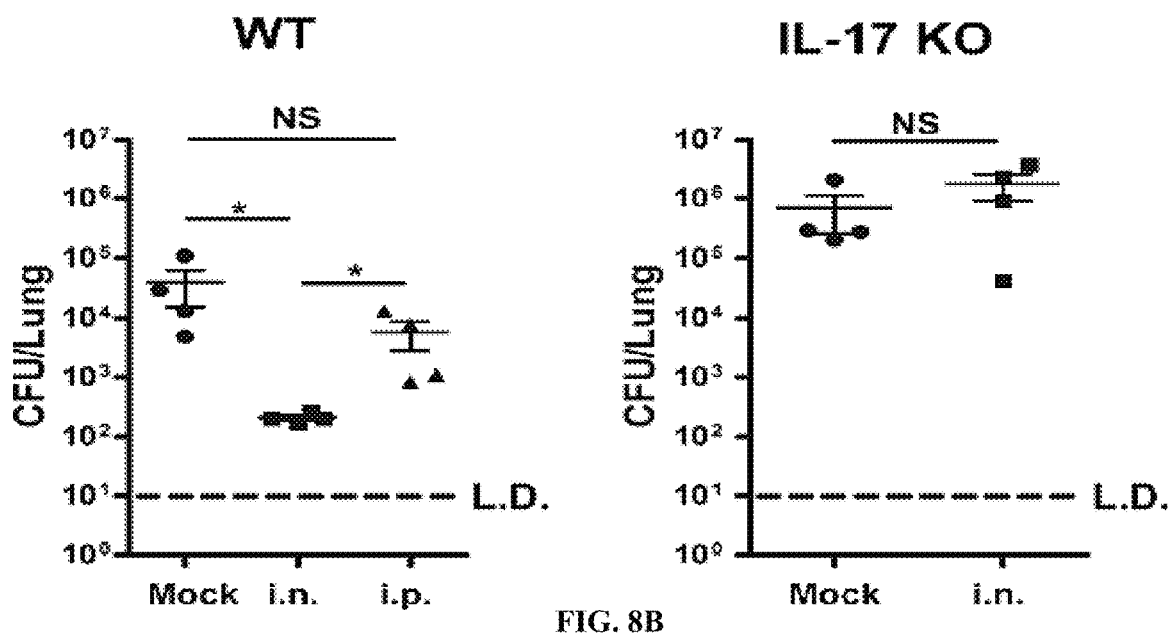

These results show that NT127 infection induces a strong, bacteria-specific CD4 T-cell response in the lung that consists of predominantly IL-17-producing Th17 cells mixed with a weak IFN-γ-producing Th1 response. To characterize the phenotypes of responding Th17 cells in the lung, intravascular staining was used with FITC-conjugated anti-CD45.2 mAb, which allowed staining of intravascular but not parenchymal lymphocytes. While total CD4 T cells in the lung were present in both intravascular and parenchymal sites, the bacteria-specific Th17 cells were predominantly in the lung parenchyma on both day 7 and day 21 after infection (FIG. 2D). On day 7, many of the bacteria-specific Th17 cells were effectors (CD69lo/CD62Llo), with some of them being TRM (CD69hi/CD62Llo). By day 21, all of the bacteria-specific Th17 cells had differentiated into the TRM-expressing CD69hi/CD62Llo phenotype. To test the role of Th17 in heterologous protection, IL-17 KO mice were immunized intranasally with heat-killed NT127 and then challenged with a heterologous strain 86-028NP. There were similar numbers of bacteria detected in the lung of immunized and unimmunized IL-17 KO mice, indicating a critical role for IL-17 in vaccine-induced protective immunity (FIG. 8B). IL-17 also played a role in host resistance to a primary NTHi lung infection, as there were more bacteria (~10-fold) in the lungs of IL-17 KO than WT mice. Furthermore, i.p. immunization in WT mice provided minimal protection against challenge with a heterologous strain (FIG. 8). Further analyses showed that i.p. immunization induced only a weak Th1 response in the spleen but did not induce a detectable Th17 response in the lung. These results indicate the importance of a local Th17 response in heterologous protection.

Example 3: Broadly Reactive Th17 Cells but Highly Strain-Specific Antibody Responses to NTHi Infection.

Figure 3A:
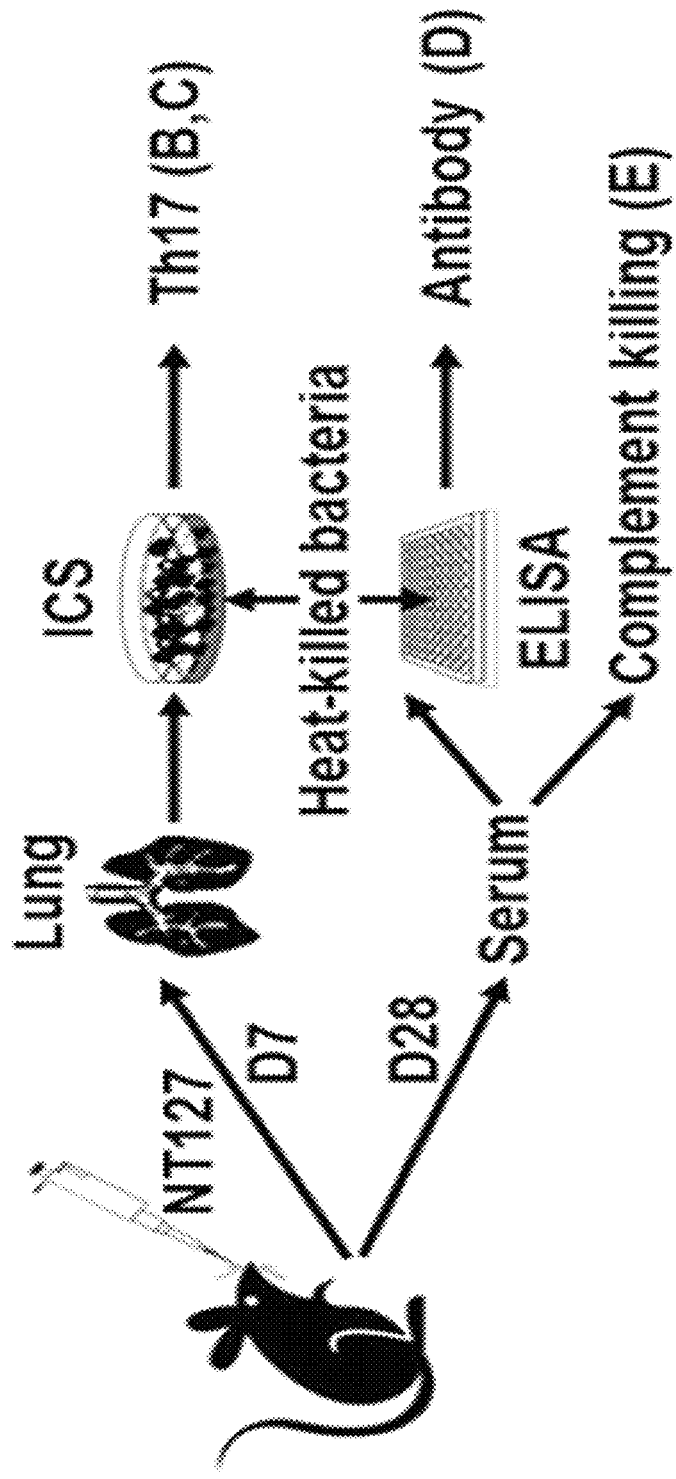
FIGS. 3A-3E are a series of graphs illustrating that Th17 cells, not antibodies, recognize heterologous strains.
Figure 3B:
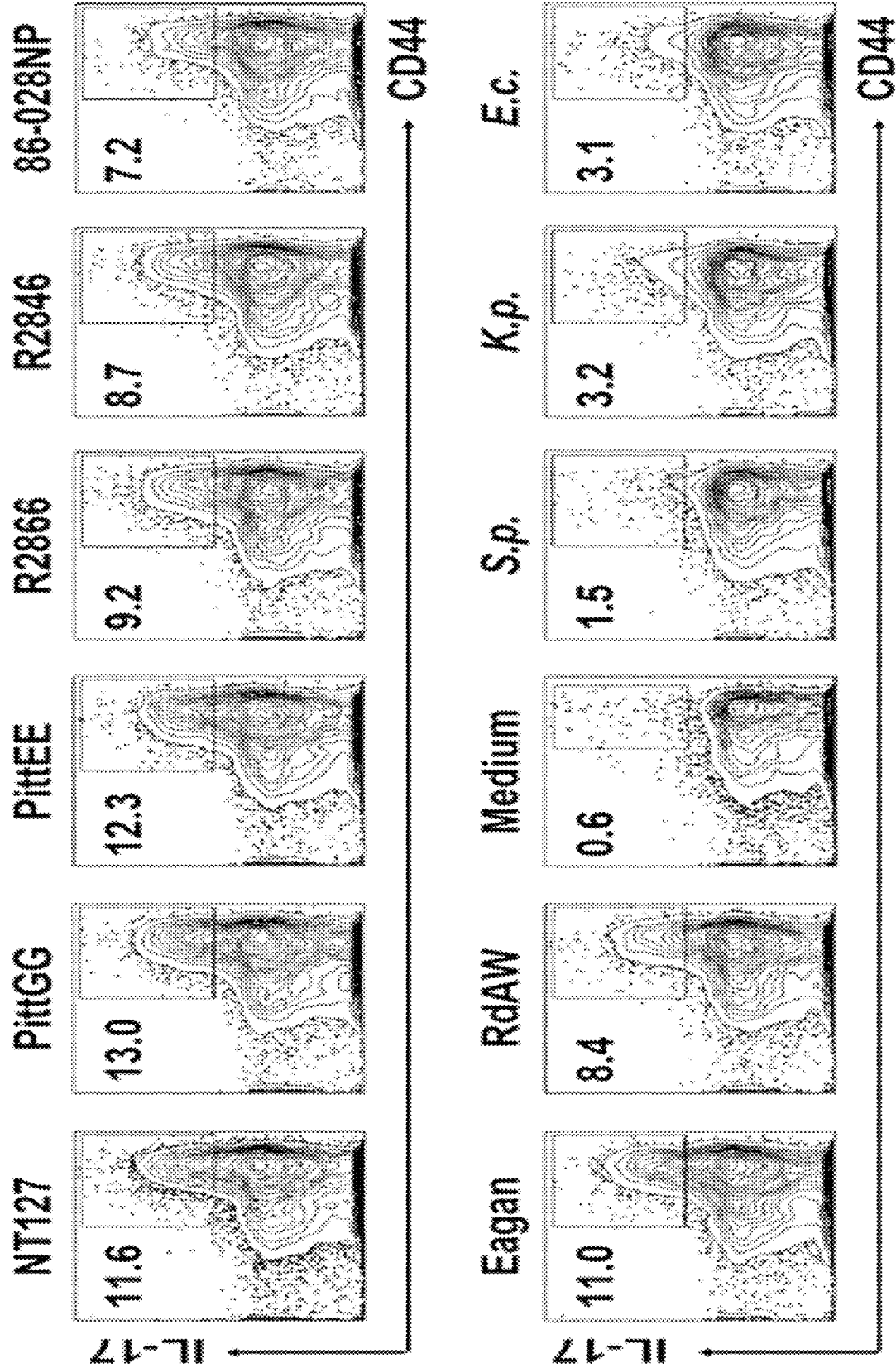
Figures 3C, 3D, 3E:
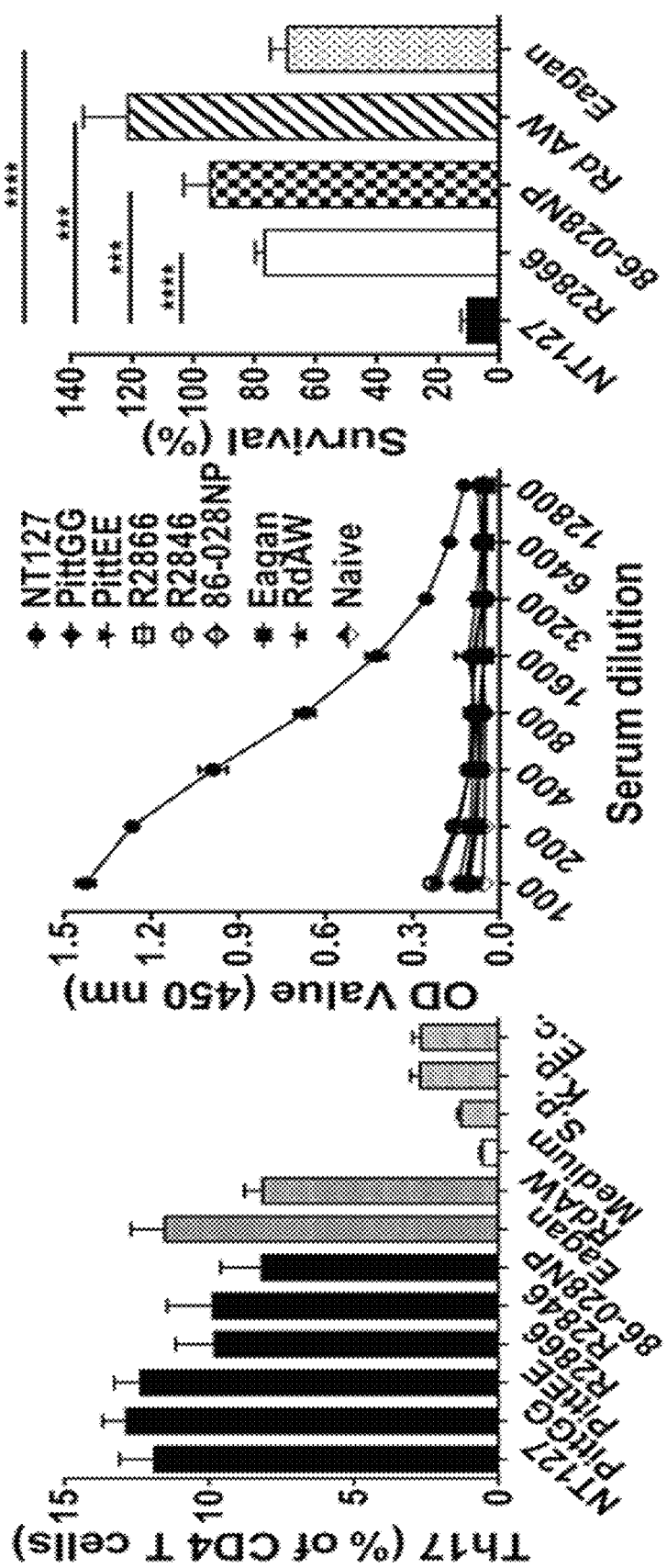
Figure 9:
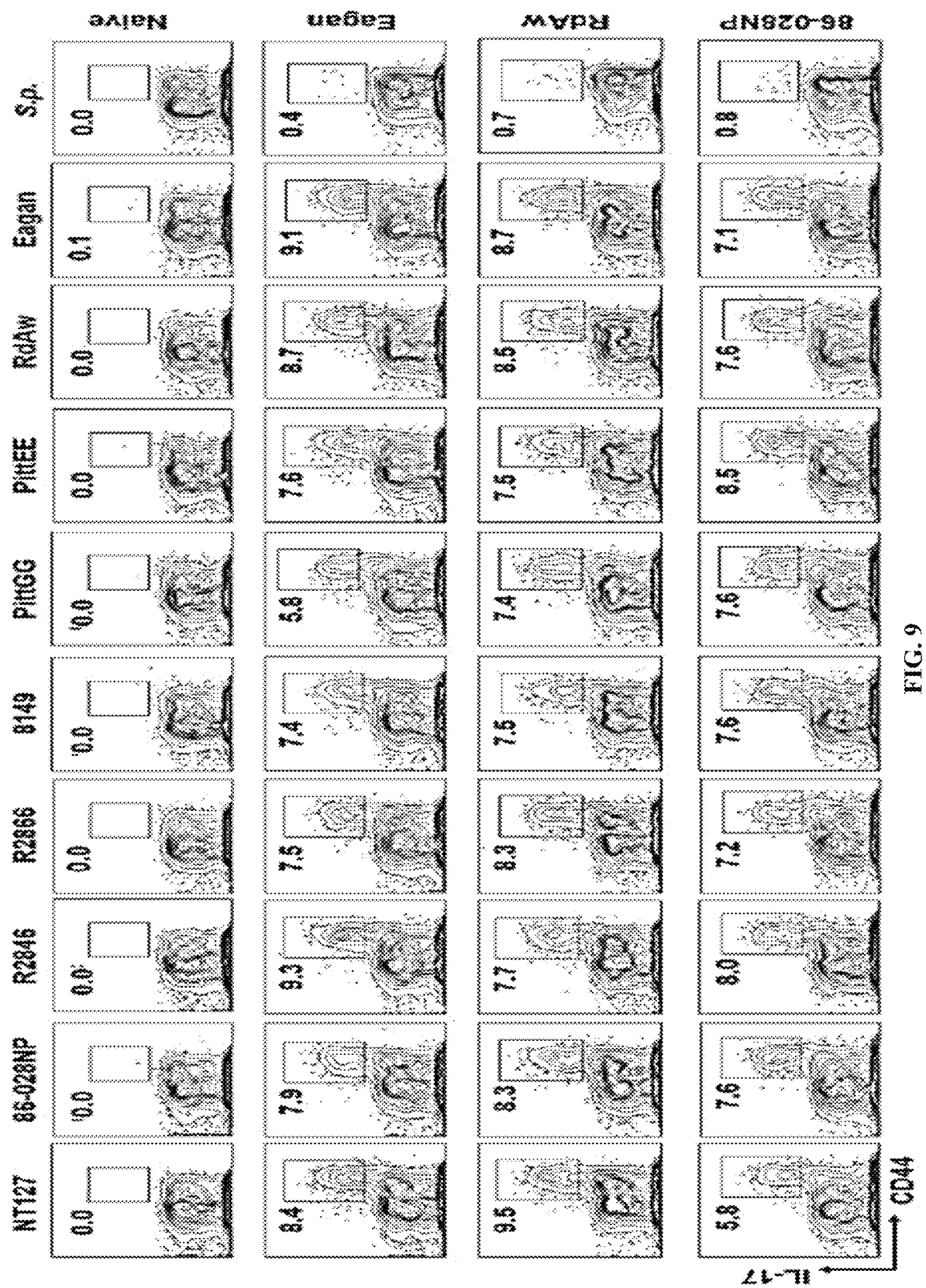
FIG. 9 is a series of graphs illustrating the broad cross-reactivity of Th17 cells. Lung lymphocytes from naïve mice and mice infected with Eagan, RdAW or 86-028NP were stimulated with heat-killed bacteria of 9 different *H. influ-* enzae strains, and *S. pneumoniae* (S.p.). Activation of reactive Th17 cells was measured by ICS of IL-17 expression.

To assess the specificity and cross-reactivity of Th17 cells, T cells from the lungs of NT127-infected mice were stimulated with heat-killed NT127 as well as heterologous NTHi strains. Similar levels of IL-17-producing CD4 T cells were detected when stimulated with NT127 or any of the other five NTHi strains tested, indicating that CD4 T cells from NT127-infected mice were capable of recognizing antigens from heterologous NTHi strains. Interestingly, Th17 cells from NT127-infected mice recognized not only heterologous NTHi strains, but also *H. influenzae* strains of encapsulated lineages (Eagan and RdAW). Similarly, Th17 cells induced by another NTHi (86-028NP) or *H. influenzae* strains of encapsulated lineages (RdAW and Eagan) were cross-reactive with all NTHi and typeable *H. influenzae* strains tested (FIG. 9). There were low levels of cross-reactivities to other bacterial species, such as *S. pneumoniae, K pneumoniae,* and *Escherichia coli* that were above the background level in the medium control (FIGS. 3B and 3C). However, the cross-reactivities to other bacterial species were much lower than the responses cross-reactive to NTHi/*H. influenzae* strains, indicating a strong NTHi/*H. influenzae*-specific Th17 response induced by NTHi infection. For comparison, specificity and cross-reactivity of antibodies induced by NT127 infection were also examined. Immune sera from NT127-infected mice were reacted with various heat-killed bacteria used as coating antigens in ELISA. While high levels of IgG specific to the homologous strain NT127 were detected, there was little cross-reactivity to the other five NTHi strains or to the two other *H. influenzae* strains (Eagan and RdAW), indicating that the antibody responses to NTHi were highly strain specific (FIG. 3D). Bactericidal activity of NT127-immune sera was further tested against different strains in complement-dependent killing assays. Anti-NT127 sera sensitized the homologous NT127 strain for complement-mediated killing (90% cfu reduction compared with naïve sera). In contrast, heterologous strains were not killed at all (for 86-028NP and RdAW strains), or only slightly (20% reduction for R2866 and Eagan strains, FIG. 3E). Together, these data indicate that the antibody response to NTHi is highly strain specific, while Th17 cells are broadly reactive, recognizing various heterologous NTHi and even encapsulated *H. influenzae*.

Example 4: A Broader Spectrum of NTHi Antigens Recognized by Th17 Cells than by Antibodies.

Figure 4A:
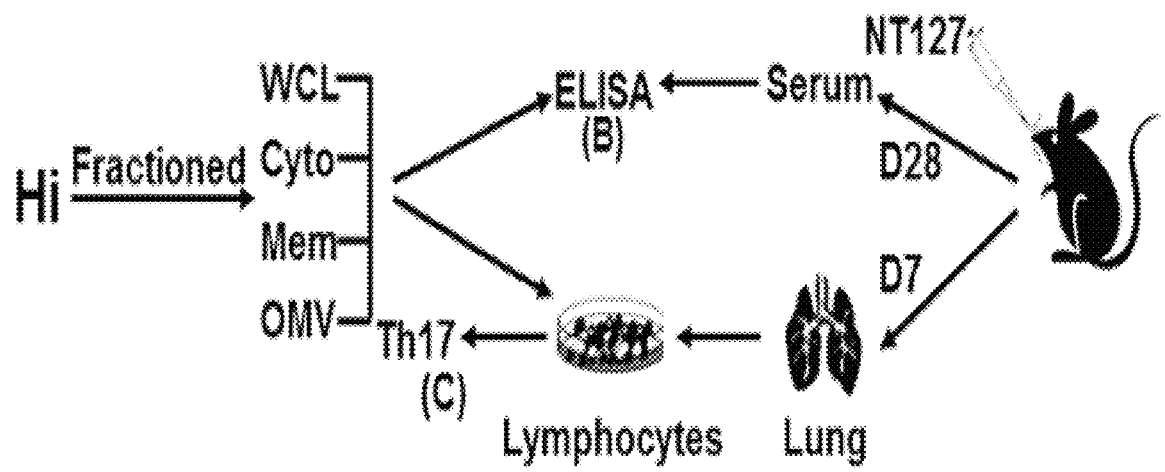
FIGS. 4A-4C are a series of graphs demonstrating that Th17 cells recognize a broader spectrum of bacterial antigens than antibodies.
Figure 4B:
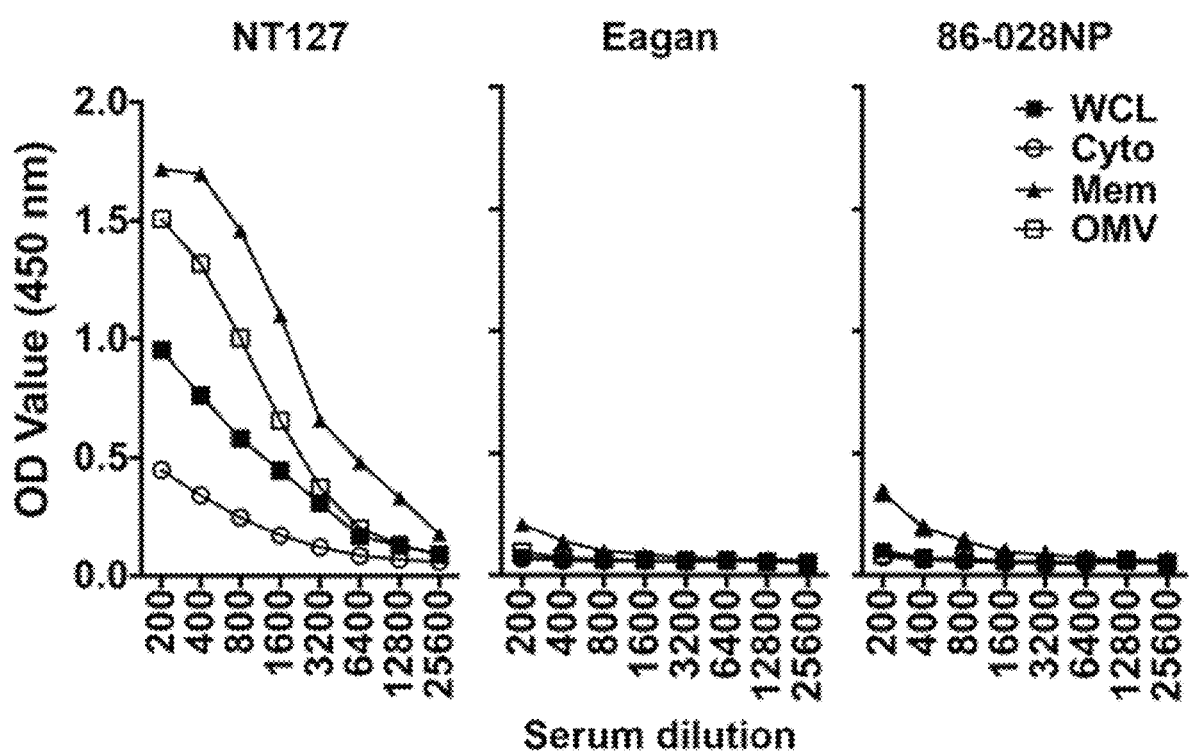
Figure 4C:
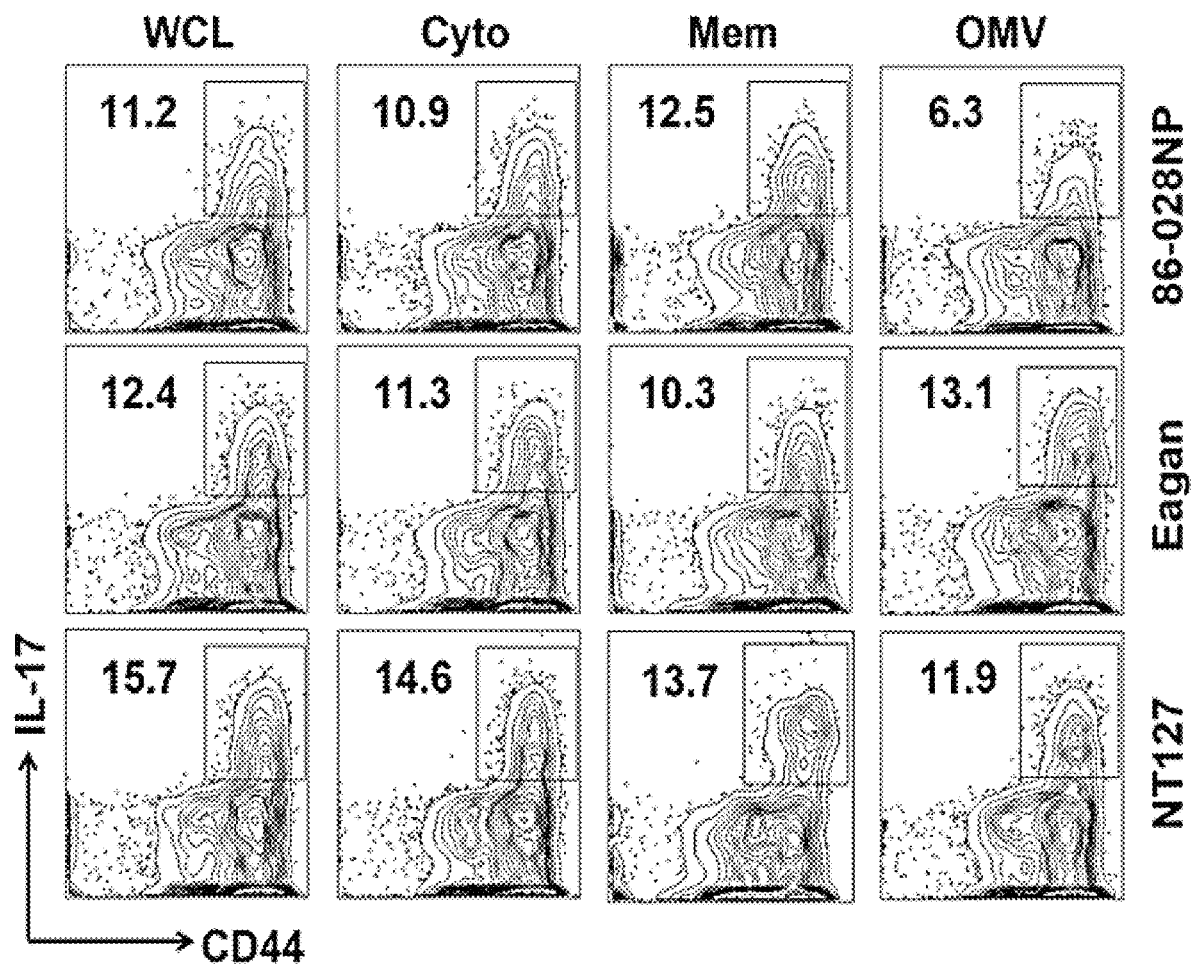

To understand why antibody responses are highly strain specific while Th17 cells are broadly reactive, the possibility that Th17 cells may recognize a broader spectrum of antigens than antibodies was tested. Bacterial proteins were separated into outer-membrane vesicles (OMVs), membrane, and cytosolic fractions, and antibody and Th17 response to these fractions was evaluated. Convalescent serum from NT127-immunized mice reacted strongly with outer-membrane vesicles and membrane fractions of NT127, to levels higher than that with whole-cell lysate (WCL), while reacting weakly with cytosolic fractions. Furthermore, protein fractions were prepared from heterologous strains (86-028NP and Eagan), and tested against serum from NT127-immunized mice. The NT127-immune serum did not react with protein fractions of either 86-028NP or Eagan (FIG. 4B), indicating little cross-recognition of conserved antigens by antibodies. Together, these results indicate that antibody recognition is focused on membrane-associated, surface antigens that are not conserved between NTHi strains, thus explaining why antibodies are highly strain specific. In contrast to the antibody responses, Th17 cells from NT127-immunized mice responded comparably to all three fractions (outer-membrane vesicles, membrane, and cytosolic fractions) isolated from NT127. Furthermore, Th17 cells from NT127-immunized mice responded to all three fractions isolated from heterologous strains (86-028NP and Eagan, FIG. 4C). Broad reactivity of Th17 cells could be due to recognition of numerous protein antigens that are conserved among NTHi strains, or nonspecific stimulation of Th17 cells by bacterial products, such as TLR ligands (lipid, cell wall components, and nucleic acids). To differentiate these two possibilities, whole-cell lysates of NT127 were treated with protease K, which resulted in complete protein digestion (FIG. 10A), and then used to stimulate Th17 cells from NT127-immunized mice. The protease treatment resulted in substantial loss of IL-17 induction (FIGS. 10B and 10C), indicating that the majority of the Th17 responses were induced by protein antigens. Together, these results show that Th17 cells recognize a broad spectrum of cytosolic and membrane-associated antigens that are conserved between NTHi strains.

Example 5: Identification of Conserved Bacterial Antigens Recognized by Th17 Cells.

Figure 5A:
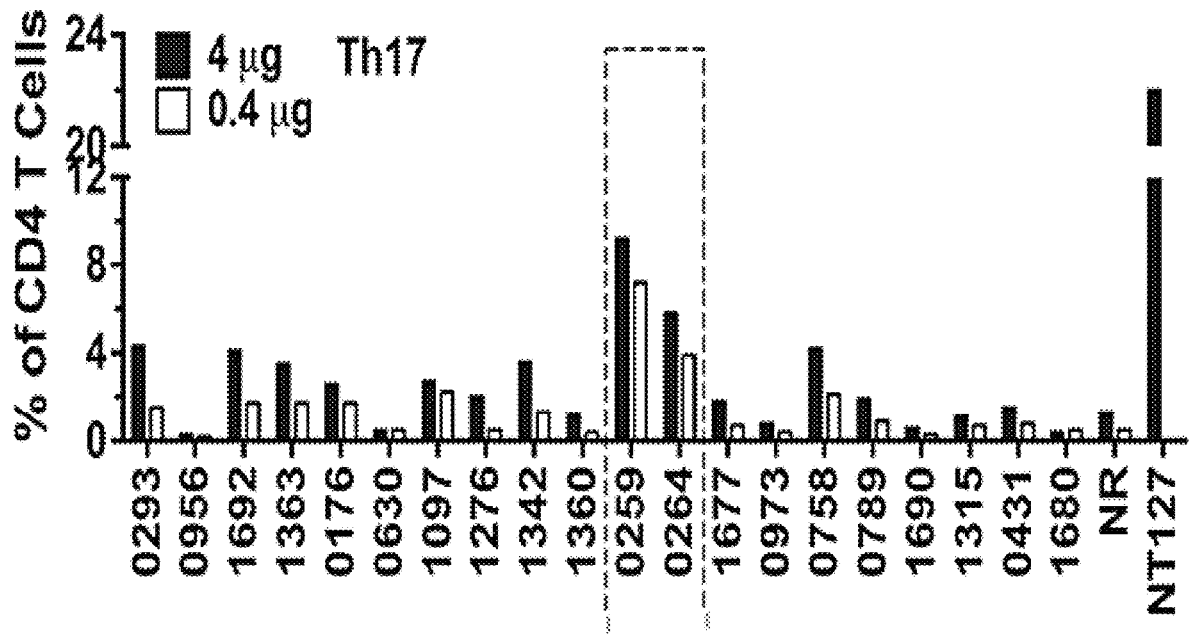
FIGS. 5A-5D are a series of graphs identifying conserved bacterial antigens recognized by Th17 cells.
Figure 5B:
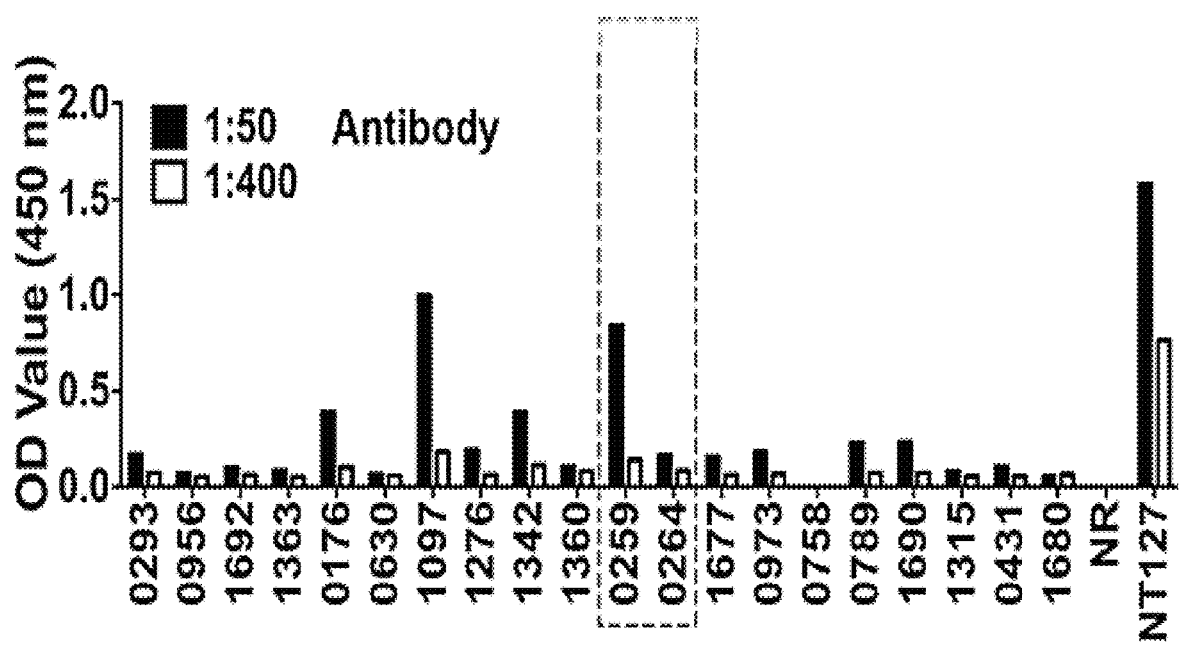
Figure 5C:
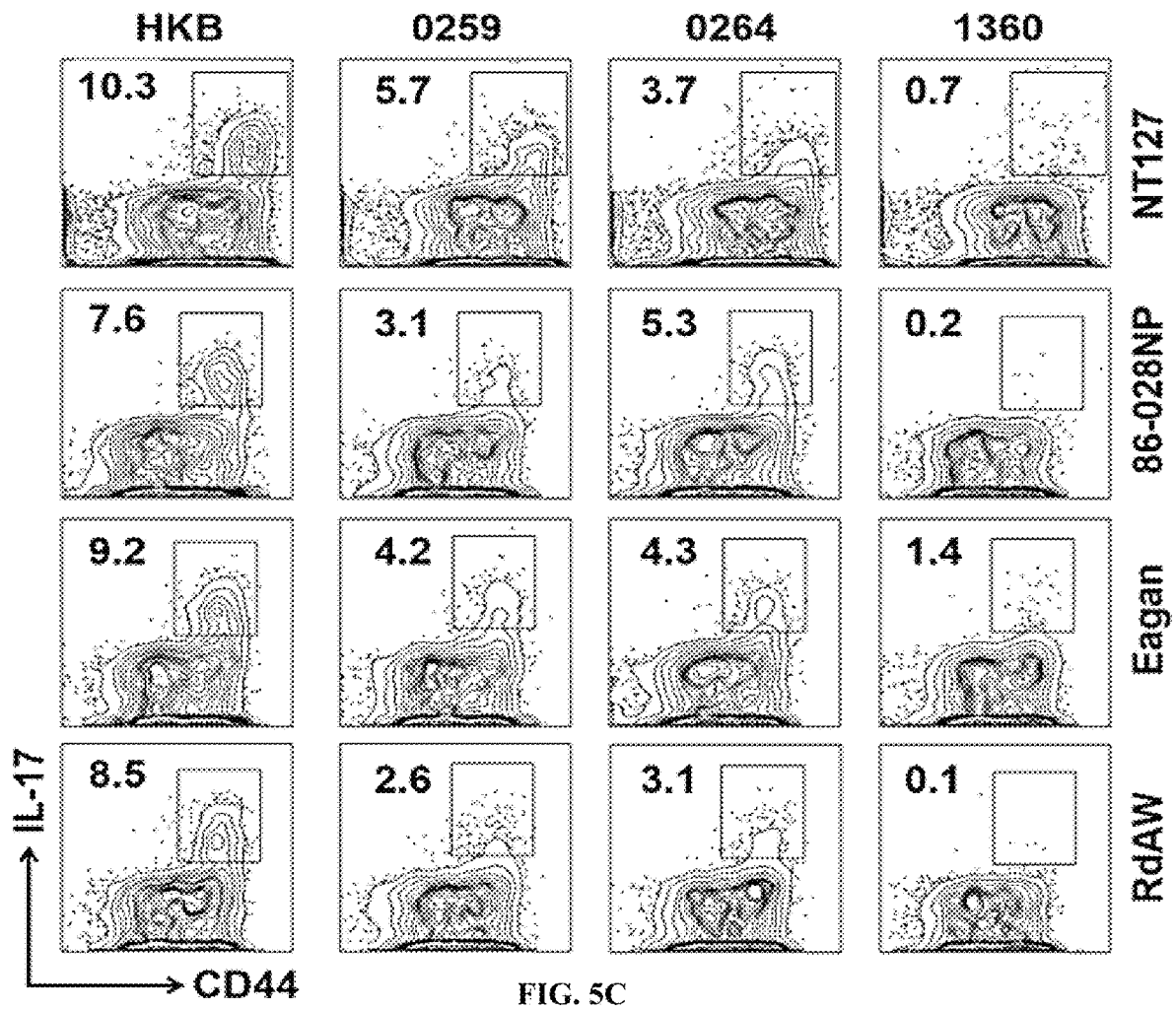
Figure 5D:
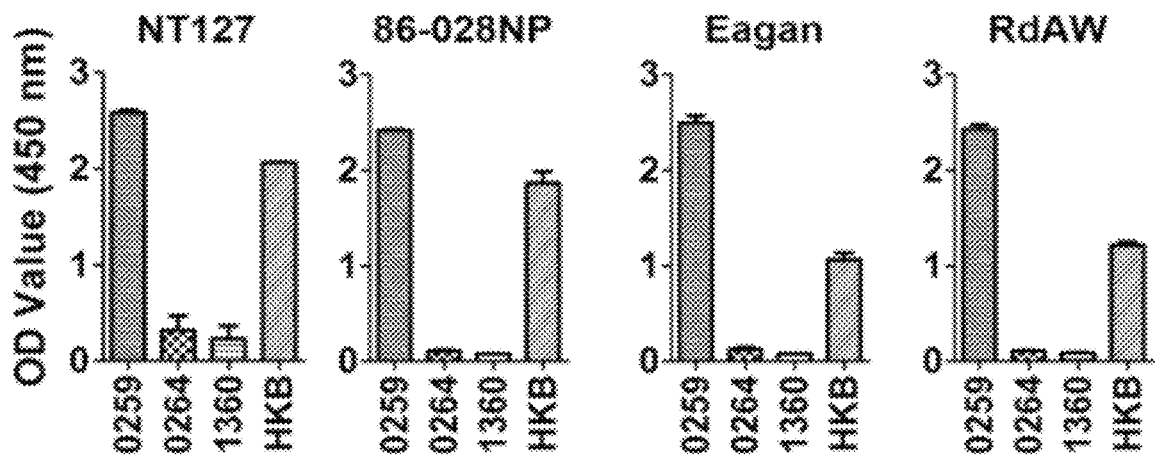

To identify conserved NTHi antigens recognized by Th17 cells, comparative genomic analyses were performed to identify a list of candidate antigens based on: (i) at least 90% amino acid similarity across sequenced NTHi genomes and (ii) no significant homology to human proteins. The list was further refined to prioritize proteins that were either previously reported to be associated with protective immunity or were identified as genes required for growth or survival of *H. influenzae* in the lung (Wong, et al. *Frontiers in Cellular and Infection Microbiology*, 2012, 2:23). In a continuous effort, candidate protein antigens were expressed, purified, and tested for recognition by Th17 cells from NT127-immunized mice. To date, 20 candidate proteins were successfully expressed to high levels in *E. coli* and purified to homogeneity by Ni2+ affinity columns (FIG. 11). Relevant characteristics of these proteins were described in FIG. 13. To screen for Th17 antigens, purified proteins were used to stimulate lung lymphocytes from NT127-infected mice in vitro and IL-17 production by CD4 T cells was determined by ICS (FIGS. 11C and 11D). Th17 responses to several proteins were detected (FIG. 5A), and the highest level of Th17 responses was induced by two proteins encoded by NT127 genes HIAG_0259 and HIAG_0264 (FIG. 13). The protein 0259 but not 0264 was also a target of antibody responses (FIG. 5B). On the other hand, protein 1097 induced a high level of the antibody response but a low level of Th17 response. Overall, among the 20 conserved proteins selected for testing, there were more proteins recognized by Th17 cells than by antibodies. The two strong Th17 antigens identified (proteins 0259 and 0264) are highly conserved among NTHi strains, with >97% homology in all strains that have been sequenced. Whether these two conserved protein antigens could be recognized by Th17 cells and antibodies from mice infected with different strains was tested, including homologous (NT127) and heterologous strains (86-028NP, Eagan, and RdAW). In all cases, both proteins were recognized by Th17, although the responses to protein 0259 were slightly lower in mice infected with the 86-028NP and RdAW strains (FIG. 5C). In contrast, only 0259 was the target of antibody responses in mice infected with the four strains tested (FIG. 5D). As controls, protein 1360 that was negative in the screen for Th17 antigens was included. As expected, protein 1360 was not recognized by lung lymphocytes from infected mice. Together, these results validate the identification of proteins 0259 and 0264 as two highly conserved antigens that are recognized by Th17 cells induced by different NTHi and encapsulated *H. influenzae*.
Example 6: Broad Protection against *H. influenzae* Infection Following Immunization with Conserved Th17 Antigens.

The potential of identified Th17 antigens as vaccine candidates for inducing broadly protective immunity was then investigated. As the first step, testing focused on a combination of the two proteins (0259 and 0264) identified to be highly immunogenic for inducing Th17 responses (FIG. 5C). Mice were immunized three times, at 1-wk intervals, intranasally with a mix of the two purified proteins and curdlan, an experimental Th17-inducing adjuvant (Zygmunt, et al. *Journal of Immunology*, 2009, 183:6933-6938), (LeibundGut-Landmann, et al. *Nature Immunology*, 2007, 8:630-638). Mice immunized with adjuvant only as well as unimmunized mice were included as controls. Three weeks after the final immunization, antigen-specific Th17 and antibody responses were measured by in vitro stimulation of lung lymphocytes and by ELISA using purified individual proteins as reacting antigens. Immunization with the two purified proteins plus adjuvant (P+A) induced high levels of Th17 cells specific to both 0259 and 0264 proteins. Interestingly, mice immunized with P+A had specific antibodies against protein 0259, but not against protein 0264 (FIG. 6A). It was next asked whether Th17 and antibodies induced by P+A immunization could recognize different bacterial strains, using heat-killed bacteria as reacting antigens in ICS and ELISA. Lung lymphocytes from P+A-immunized mice responded to all three strains tested (NT127, 82866, and Eagan) and produced IL-17, as measured by ICS. In contrast, sera from P+A-immunized mice did not react with heat-killed intact bacteria of NT127, 82866, and Eagan used as coating antigens in ELISA. As expected, no antigen-specific Th17 and antibody responses were detected in unimmunized mice and mice immunized with adjuvant only (FIG. 6B). Together, these results show that immunization with protein antigens of 0259 and 0264 induces antigen-specific Th17 cells to both proteins, and these Th17 cells are capable of recognizing different bacterial strains. On the other hand, only protein 0259-specific antibodies are induced, yet these antibodies fail to bind to intact bacteria of any strains tested, presumably because antibody epitopes of protein 0259 are not exposed on the surface of intact bacteria. To test protective immunity, immunized mice were challenged with NT127, 82866, or Eagan by intranasal inoculation under anesthesia, resulting in direct infection of the lower respiratory tract. Two days after bacterial challenge, P+A-immunized mice had significantly lower numbers of bacteria (100- to 1,000-fold) in the lung compared with animals immunized with the adjuvant only or left unimmunized (FIG. 6C). Importantly, protection was evident against not only NTHi strains (NT127 and R2866), but also the encapsulated, highly virulent Eagan strain.

To determine the role of antibodies and T cells in vaccine-induced protection, sera and CD4 T cells harvested from P+A immunized mice were transferred to naive recipients and then recipient mice were challenged with NT127. On day 2 after NT127 challenge, bacterial loads in mice that received immune sera were not significantly different from those in control mice infected with NT127. On the other hand, mice that received CD4 T cells were protected, with 2-log lower bacterial loads in the lung (FIG. 6D). Together, these results show that conserved antigens recognized by Th17 cells induce protection against lung infection by different NTHi and encapsulated *H. influenzae* strains. Inclusion of Th17 antigens in subunit vaccines may help overcome the limitation of current antibody-based approaches by inducing broadly protective immunity.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of immunizing a subject against *Haemophilus influenzae*, the method comprising administering to the subject an effective amount of a composition comprising *H. influenzae* oligopeptide binding protein A (OppA) and *H. influenzae* lipopolysaccharide assembly protein B (LapB).

2. The method of claim 1, wherein administering the composition elicits a T helper 17 (Th17) response.

3. The method of claim 1, wherein the OppA and/or LapB is derived from a nontypeable *H. influenzae* (NTHi) strain.

4. The method of claim 3, wherein the NTHi strain is NT127.

5. The method of claim 3, wherein the OppA comprises the amino acid sequence of SEQ ID NO:2.

6. The method of claim 3, wherein the OppA is encoded by the nucleotide sequence of SEQ ID NO:1.

7. The method of claim 3, wherein the LapB comprises the amino acid sequence of SEQ ID NO: 4.

8. The method of claim 3, wherein the LapB is encoded by the nucleotide sequence of SEQ ID NO: 3.

9. The method of claim 1, wherein the subject is a human.

10. The method of claim 1, wherein the composition further comprises an immunogenic adjuvant.

11. The method of claim 10, wherein the immunogenic adjuvant is selected from the group consisting of alum, MF59, AS03, Virosome, and AS04.

12. The method of claim 1, wherein the *H. influenzae* infection is selected from the group consisting of otitis media, community-acquired pneumonia (CAP), conjunctivitis, sinusitis, meningitis, and exacerbation of chronic obstructive pulmonary disease (COPD).

13. The method of claim 1, wherein the subject is at risk for *H. influenzae* due to having a comorbidity.

14. The method of claim 13, wherein the comorbidity is selected from the group consisting of a viral infection, a bacterial infection, a parasite, a fungal infection, and an immuno-compromised state.

15. The method of claim 14, wherein the viral infection is an influenza infection.

16. The method of claim 1, wherein the method of immunizing is cross-protective against multiple *H. influenzae* strains.

17. The method of claim 16, wherein the *H. influenzae* strains are selected from the group consisting of type A serotype, type B serotype, type C serotype, type D serotype, type E serotype, type F serotype, and any NTHi strain.

18. A method of treating a subject at risk for developing a *H. influenzae* infection, the method comprising administering to the subject an effective amount of a composition comprising *H. influenzae* protein OppA and *H. influenzae* protein LapB.

19. The method of claim 18, wherein administering the composition elicits a T helper 17 (Th17) response.

20. The method of claim 18, wherein the OppA and/or LapB is derived from a nontypeable *H. influenzae* (NTHi) strain.

21. The method of claim 20, wherein the NTHi strain is NT127.

22. The method of claim 20, wherein the OppA comprises the amino acid sequence of SEQ ID NO:2.

23. The method of claim 20, wherein the OppA is encoded by the nucleotide sequence of SEQ ID NO:1.

24. The method of claim 20, wherein the LapB comprises the amino acid sequence of SEQ ID NO: 4.

25. The method of claim 20, wherein the LapB is encoded by the nucleotide sequence of SEQ ID NO: 3.

26. The method of claim 18, wherein the subject is a human.

27. The method of claim 18, wherein the composition further comprises an immunogenic adjuvant.

28. The method of claim 27, wherein the immunogenic adjuvant is selected from the group consisting of alum, MF59, AS03, Virosome, and AS04.

29. The method of claim 18, wherein the *H. influenzae* infection is selected from the group consisting of otitis media, community-acquired pneumonia (CAP), conjunctivitis, sinusitis, meningitis, and exacerbation of chronic obstructive pulmonary disease (COPD).

30. The method of claim 18, wherein the subject is at risk for *H. influenzae* due to having a comorbidity.

31. The method of claim 30, wherein the comorbidity is selected from the group consisting of a viral infection, a bacterial infection, a parasite, a fungal infection, and an immuno-compromised state.

32. The method of claim 31, wherein the viral infection is an influenza infection.

33. The method of claim 18, wherein the method of treating is cross-protective against multiple *H. influenzae* strains.

34. The method of claim 33, wherein the *H. influenzae* strains are selected from the group consisting of type A serotype, type B serotype, type C serotype, type D serotype, type E serotype, type F serotype, and any NTHi strain.

35. A method of treating a subject, wherein the subject is infected with *H. influenza*, the method comprising administering to the subject an effective amount of a composition comprising *H. influenzae* protein OppA and *H. influenzae* protein LapB.

36. The method of claim 35, wherein administering the composition elicits a T helper 17 (Th17) response.

37. The method of claim 35, wherein the OppA and/or LapB is derived from a nontypeable *H. influenzae* (NTHi) strain.

38. The method of claim 37, wherein the NTHi strain is NT127.

39. The method of claim 37, wherein the OppA comprises the amino acid sequence of SEQ ID NO:2.

40. The method of claim 37, wherein the OppA is encoded by the nucleotide sequence of SEQ ID NO:1.

41. The method of claim 37, wherein the LapB comprises the amino acid sequence of SEQ ID NO: 4.

42. The method of claim 37, wherein the LapB is encoded by the nucleotide sequence of SEQ ID NO: 3.

43. The method of claim 35, wherein the subject is a human.

44. The method of claim 35, wherein the composition further comprises an immunogenic adjuvant.

45. The method of claim 44, wherein the immunogenic adjuvant is selected from the group consisting of alum, MF59, AS03, Virosome, and AS04.

46. The method of claim 35, wherein the *H. influenzae* infection is selected from the group consisting of otitis media, community-acquired pneumonia (CAP), conjunctivitis, sinusitis, meningitis, and exacerbation of chronic obstructive pulmonary disease (COPD).

47. The method of claim 35, wherein the subject has a comorbidity.

48. The method of claim 47, wherein the comorbidity is selected from the group consisting of a viral infection, a bacterial infection, a parasite, a fungal infection, and an immuno-compromised state.

49. The method of claim 48, wherein the viral infection is an influenza infection.

50. The method of claim 35, wherein the method of treating is cross-protective against multiple *H. influenzae* strains.

51. The method of claim 50, wherein the *H. influenzae* strains are selected from the group consisting of type A serotype, type B serotype, type C serotype, type D serotype, type E serotype, type F serotype, and any NTHi strain.

* * * * *

SEQUENCE LISTING

```
<160> NUMBER OF SEQ ID NOS: 49

<210> SEQ ID NO 1
<211> LENGTH: 1623
<212> TYPE: DNA
<213> ORGANISM: Haemophilus influenzae
<220> FEATURE:
<221> NAME/KEY: misc_feature
<222> LOCATION: (565)..(565)
<223> OTHER INFORMATION: n is a, c, g, or t

<400> SEQUENCE: 1
atgcaacaca aactactctt ctctgcaatc gctcttgccc tttcctattc tgcgcaagca      60
gttatagtgc ctgaaggaac acaattagat gaaaaacaac atatcgtcat caataacggg     120
gctgaaccgc aaagtttga cccacacaaa accgaaggtg tgccagaatc taacgttgct     180
tatcaattac ttgaaggctt agtcacctca gactctgaag gtaaacttca accgggtgcg     240
gctgaaagct gggaaaatac acctgacttc aaaacctgga cattccattt acgtaaagat     300
```

```
gctaaatggt caaacggaga tcctgttact gcacacgatt tcgtgtttgc gtggcgtcgt    360
ttagtggatc ctgcaactgc tgcaccttac gcgagttacc taagttattt acaagttgaa    420
aatgcacaag acattattga cggtaagaaa aaaccggctg aattaggcgt ggaacaaaag    480
atgattacac ctttgtggtt catacaacca atcctgtgcc ttatacagtc agtttcgact    540
caccaatcct tattgccatt accanaaaaa gtagtcgaaa aattgggtga tgcatgggtg    600
aaaaaagaaa actacgtggg taacggtgcg tataagctgg ctaaccacat cattaacgaa    660
aaaatcgaat ttgaacgtaa cccactttat tggaacgata agaaaccgt aatcaatagc     720 gcgacattcc tcgccattga aaacccaagt accgatgtag cgcgttatcg tgcgggcgat    780
ttagacatga ccagttatgg tttaccgcca gaacaattcg ctaaattaca aaagaattg     840 ccaggcgaag tatacgttac tcgtaccc ta ggaacttatt cttatgaatt aaacaataag    900
aaagcacctt ttgataacgt gaatattcgt aaagccttga acttatccct tgatcgtaat    960
gtgatcaccg ataaagtatt gggtcaaggt caaacaccaa cctatgtgtt taccccaact   1020
tacatcgaag aaggtcatct cattcaacaa cctgcttatt caaaagaacc gatggcacaa   1080
cgtaatgaag aagccattaa actcttagaa gaagctggtt acagtaaagc gaatccgttg   1140
aaattcagca ttctttataa taccaatgaa accacaaaaa agtggctat tgctgcagca    1200 tctatgtgga agctaacac caaaggtttg attgacgtga attagaaaa ccaagagtgg     1260 aaaacttaca ttgatagccg tcgtgcaggt cgttacgatg tggcgcgtgc tggatggaat   1320
gcggattaca accaagcaac aacattcggc aactatttct tatctaattc tagtaacaat   1380
accgcgaaat atgcgaatcc agaatatgat aaagcgatgg cagaatctta cgcagcaacg   1440
gatgcagaag gtcgtgcaaa agcttatgcg aaagccgaag aaattcttgg aaaagattac   1500
ggtatcgtac caatctttaa ctatgtgaat ccacgcttag tgaaaccta cgtaaaaggt    1560 tattcaggca agatccaca agatcatatt tacttacgca atctttatat tattaaacat    1620
taa                                                                 1623
```

<210> SEQ ID NO 2
<211> LENGTH: 537
<212> TYPE: PRT
<213> ORGANISM: Haemophilus influenzae

<400> SEQUENCE: 2

```
Met Gln His Lys Leu Leu Phe Ser Ala Ile Ala Leu Ala Leu Ser Tyr
1               5                   10                  15

Ser Ala Gln Ala Val Ile Val Pro Glu Gly Thr Gln Leu Asp Glu Lys
                20                  25                  30

Gln His Ile Val Ile Asn Asn Gly Ala Glu Pro Gln Ser Phe Asp Pro
            35                  40                  45

His Lys Thr Glu Gly Val Pro Glu Ser Asn Val Ala Tyr Gln Leu Leu
        50                  55                  60

Glu Gly Leu Val Thr Ser Asp Ser Glu Gly Lys Leu Gln Pro Gly Ala
65                  70                  75                  80

Ala Glu Ser Trp Glu Asn Thr Pro Asp Phe Lys Thr Trp Thr Phe His
                85                  90                  95

Leu Arg Lys Asp Ala Lys Trp Ser Asn Gly Asp Pro Val Thr Ala His
                100                 105                 110

Asp Phe Val Phe Ala Trp Arg Arg Leu Val Asp Pro Ala Thr Ala Ala
            115                 120                 125

Pro Tyr Ala Ser Tyr Leu Ser Tyr Leu Gln Val Glu Asn Ala Gln Asp
```

```
            130                 135                 140
Ile Ile Asp Gly Lys Lys Pro Ala Glu Leu Gly Val Glu Lys Asp
145                 150                 155                 160

Asp Tyr Thr Phe Val Val His Thr Thr Asn Pro Val Pro Tyr Thr Val
                    165                 170                 175

Ser Thr His Gln Ser Leu Leu Pro Leu Pro Lys Val Val Glu Lys Leu
                    180                 185                 190

Gly Asp Ala Trp Val Lys Lys Glu Asn Tyr Val Gly Asn Gly Ala Tyr
                    195                 200                 205

Lys Leu Ala Asn His Ile Ile Asn Glu Lys Ile Glu Phe Glu Arg Asn
210                 215                 220

Pro Leu Tyr Trp Asn Asp Lys Glu Thr Val Ile Asn Ser Ala Thr Phe
225                 230                 235                 240

Leu Ala Ile Glu Asn Pro Ser Thr Asp Val Ala Arg Tyr Arg Ala Gly
                    245                 250                 255

Asp Leu Asp Met Thr Ser Tyr Gly Leu Pro Pro Glu Gln Phe Ala Lys
                    260                 265                 270

Leu Gln Lys Glu Leu Pro Gly Glu Val Tyr Val Thr Arg Thr Leu Gly
                    275                 280                 285

Thr Tyr Ser Tyr Glu Leu Asn Asn Lys Lys Ala Pro Phe Asp Asn Val
290                 295                 300

Asn Ile Arg Lys Ala Leu Asn Leu Ser Leu Asp Arg Asn Val Ile Thr
305                 310                 315                 320

Asp Lys Val Leu Gly Gln Gly Gln Thr Pro Thr Tyr Val Phe Thr Pro
                    325                 330                 335

Thr Tyr Ile Glu Glu Gly His Leu Ile Gln Gln Pro Ala Tyr Ser Lys
                    340                 345                 350

Glu Pro Met Ala Gln Arg Asn Glu Ala Ile Lys Leu Leu Glu Glu
                355                 360                 365

Ala Gly Tyr Ser Lys Ala Asn Pro Leu Lys Phe Ser Ile Leu Tyr Asn
    370                 375                 380

Thr Asn Glu Asn His Lys Lys Val Ala Ile Ala Ala Ser Met Trp
385                 390                 395                 400

Lys Ala Asn Thr Lys Gly Leu Ile Asp Val Lys Leu Glu Asn Gln Glu
                    405                 410                 415

Trp Lys Thr Tyr Ile Asp Ser Arg Arg Ala Gly Arg Tyr Asp Val Ala
                    420                 425                 430

Arg Ala Gly Trp Asn Ala Asp Tyr Asn Gln Ala Thr Thr Phe Gly Asn
                    435                 440                 445

Tyr Phe Leu Ser Asn Ser Ser Asn Asn Thr Ala Lys Tyr Ala Asn Pro
    450                 455                 460

Glu Tyr Asp Lys Ala Met Ala Glu Ser Tyr Ala Ala Thr Asp Ala Glu
465                 470                 475                 480

Gly Arg Ala Lys Ala Tyr Ala Lys Ala Glu Glu Ile Leu Gly Lys Asp
                    485                 490                 495

Tyr Gly Ile Val Pro Ile Phe Asn Tyr Val Asn Pro Arg Leu Val Lys
                    500                 505                 510

Pro Tyr Val Lys Gly Tyr Ser Gly Lys Asp Pro Gln Asp His Ile Tyr
                    515                 520                 525

Leu Arg Asn Leu Tyr Ile Ile Lys His
    530                 535

<210> SEQ ID NO 3
```

```
<211> LENGTH: 879
<212> TYPE: DNA
<213> ORGANISM: Haemophilus influenzae

<400> SEQUENCE: 3
atggcaatcc agatgacaac aaaaacaact taccaatggc ctcaatctaa ggatatttat      60
ccatatcgac cagggcgttt tgatgcacca aaacattggc gttataactt acgtagcttt     120
ttaaatcgtg gttcaattcg tcgctttgaa caatttatca atcagcatcc ttttctcatc     180
gatattttta atacgcactt ggattatagt tatcctgttg cttgtcgttt tttagataag     240
cgttttaacg catcacagcg ttttcatgcg gtttgtgaga atcttttatt tttacccgaa     300
aaacttaccg cactttctac gccgttatgg gaaaaacctc taagttttgg cgaagtcatt     360
cctgattttg aaatgacatt aagcatgaca acccatcaac cgatggaagg atattgggta     420
ttggagctat ggcataaacc aagaaacgaa ttagtctatt tgcttacttt tgccaaattg     480
ggcgatgcgt tgcttattgc tgttgtacaa gggccaaatt ttgaaggctc aaaggaaatg     540
gtgaaacaac taaccaaatt atgccacggt ttacgccctg cctatttaat ggttgaaacc     600
atgaaatcac tcacaaaaat actaggctac aataaattgc tgggcattcc acaaaaatac     660 caaataaat ctcgtttcat ccaaagcaaa caatatacag tggactatga tgcaattttt     720
ggcgaatcag gcggagaatt aaaagattac tgggaattgc ctttagaaat ggatagaaat     780
ctagatgata ttccaagtaa aaaacgttcc atgtatcgta agcgttatgc gatgctagat     840
gatttggcta aggtaattga agaaaagtta ggattgtaa                            879

<210> SEQ ID NO 4
<211> LENGTH: 292
<212> TYPE: PRT
<213> ORGANISM: Haemophilus influenzae

<400> SEQUENCE: 4

Met Ala Ile Gln Met Thr Thr Lys Thr Thr Tyr Gln Trp Pro Gln Ser
1               5                   10                  15

Lys Asp Ile Tyr Pro Tyr Arg Pro Gly Arg Phe Asp Ala Pro Lys His
            20                  25                  30

Trp Arg Tyr Asn Leu Arg Ser Phe Leu Asn Arg Gly Ser Ile Arg Arg
        35                  40                  45

Phe Glu Gln Phe Ile Asn Gln His Pro Phe Leu Ile Asp Ile Phe Asn
    50                  55                  60

Thr His Leu Asp Tyr Ser Tyr Pro Val Ala Cys Arg Phe Leu Asp Lys
65                  70                  75                  80

Arg Phe Asn Ala Ser Gln Arg Phe His Ala Val Cys Glu Asn Leu Leu
                85                  90                  95

Phe Leu Pro Glu Lys Leu Thr Ala Leu Ser Thr Pro Leu Trp Glu Lys
            100                 105                 110

Pro Leu Ser Phe Gly Glu Val Ile Pro Asp Phe Glu Met Thr Leu Ser
        115                 120                 125

Met Thr Thr His Gln Pro Met Glu Gly Tyr Trp Val Leu Glu Leu Trp
    130                 135                 140

His Lys Pro Arg Asn Glu Leu Val Tyr Leu Leu Thr Phe Ala Lys Leu
145                 150                 155                 160

Gly Asp Ala Leu Leu Ile Ala Val Val Gln Gly Pro Asn Phe Glu Gly
                165                 170                 175

Ser Lys Glu Met Val Lys Gln Leu Thr Lys Leu Cys His Gly Leu Arg
            180                 185                 190
```

```
Pro Ala Tyr Leu Met Val Glu Thr Met Lys Ser Leu Thr Lys Ile Leu
        195                 200                 205

Gly Tyr Asn Lys Leu Leu Gly Ile Pro Gln Lys Tyr Gln Asn Lys Ser
    210                 215                 220

Arg Phe Ile Gln Ser Lys Gln Tyr Thr Val Asp Tyr Asp Ala Ile Phe
225                 230                 235                 240

Gly Glu Ser Gly Gly Glu Leu Lys Asp Tyr Trp Glu Leu Pro Leu Glu
                245                 250                 255

Met Asp Arg Asn Leu Asp Asp Ile Pro Ser Lys Lys Arg Ser Met Tyr
            260                 265                 270

Arg Lys Arg Tyr Ala Met Leu Asp Asp Leu Ala Lys Val Ile Glu Glu
        275                 280                 285

Lys Leu Gly Leu
    290
```

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
gggccatggt gcaacacaaa ctactct     27

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
gggctcgaga tgtttaataa tataaag     27

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
gggccatggt gacaacaaaa acaact      26

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
cggctcgagc aatcctaact tttcttc     27

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
ggcccatggt gcgattttct aaact                                              25

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
ggcctcgagc accccataaa caaag                                              25

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
gcgccatgga tggggtggat tatat                                              25

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
gcgctcgagg aagctataaa ctgcact                                            27

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
gggccatggt gaaaaacatc gcaaaagt                                           28

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
gggctcgagt ttttctctt gtgct                                               25

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
gggccatggt gaaaaaaaca acctt                                              25

<210> SEQ ID NO 16
<211> LENGTH: 26
<212> TYPE: DNA

```
<213> ORGANISM: Artificial Sequence
<220> FEATURE:
<223> OTHER INFORMATION: primer

<400> SEQUENCE: 16
gggctcgagt tttttacgtt gatcat                                          26

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
gggccatggt gctcgcaaaa ttgtt                                           25

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
gggctcgaga gttttacctt cagc                                            24

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
gggctcgaga gttttacctt cagc                                            24

<210> SEQ ID NO 20
<211> LENGTH: 28
<212> TYPE: DNA
<213> ORGANISM: Artificial Sequence
<220> FEATURE:
<223> OTHER INFORMATION: primer

<400> SEQUENCE: 20
ggggcggccg ccttcgcaat acgtttat                                        28

<210> SEQ ID NO 21
<211> LENGTH: 28
<212> TYPE: DNA
<213> ORGANISM: Artificial Sequence
<220> FEATURE:
<223> OTHER INFORMATION: primer

<400> SEQUENCE: 21
gcgccatggt gaaaaaactt ttaaaaat                                        28

<210> SEQ ID NO 22
<211> LENGTH: 28
<212> TYPE: DNA
<213> ORGANISM: Artificial Sequence
<220> FEATURE:
<223> OTHER INFORMATION: primer

<400> SEQUENCE: 22
gcgctcgagt ttagctaaac attctatg                                        28
```

<210> SEQ ID NO 23
<211> LENGTH: 26
<212> TYPE: DNA
<213> ORGANISM: Artificial Sequence
<220> FEATURE:
<223> OTHER INFORMATION: primer

<400> SEQUENCE: 23
ggcctcgaga acattttcta ccgcct                                26

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
cgcccatggt gaatatcaca gccat                                 25

<210> SEQ ID NO 25
<211> LENGTH: 26
<212> TYPE: DNA
<213> ORGANISM: Artificial Sequence
<220> FEATURE:
<223> OTHER INFORMATION: primer

<400> SEQUENCE: 25
ggcctcgagt ttatccttat tttgac                                26

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
cgcccatggt gatcgtcaat tttat                                 25

<210> SEQ ID NO 27
<211> LENGTH: 27
<212> TYPE: DNA
<213> ORGANISM: Artificial Sequence
<220> FEATURE:
<223> OTHER INFORMATION: primer

<400> SEQUENCE: 27
gccctcgaga cctgcgccaa acataat                               27

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
cgcccatggt gatcgtcaat tttat                                 25

<210> SEQ ID NO 29
<211> LENGTH: 27
<212> TYPE: DNA
<213> ORGANISM: Artificial Sequence
<220> FEATURE:

<223> OTHER INFORMATION: primer

<400> SEQUENCE: 29
gccctcgaga cctgcgccaa acataat                                              27

<210> SEQ ID NO 30
<211> LENGTH: 27
<212> TYPE: DNA
<213> ORGANISM: Artificial Sequence
<220> FEATURE:
<223> OTHER INFORMATION: primer

<400> SEQUENCE: 30
ccggctagca tggcaaccta cttttct                                              27

<210> SEQ ID NO 31
<211> LENGTH: 28
<212> TYPE: DNA
<213> ORGANISM: Artificial Sequence
<220> FEATURE:
<223> OTHER INFORMATION: primer

<400> SEQUENCE: 31
gcgctcgagt tatttcactt ctttaaat                                             28

<210> SEQ ID NO 32
<211> LENGTH: 26
<212> TYPE: DNA
<213> ORGANISM: Artificial Sequence
<220> FEATURE:
<223> OTHER INFORMATION: primer

<400> SEQUENCE: 32
ccgccatggg ccaaaatgct aaacgt                                               26

<210> SEQ ID NO 33
<211> LENGTH: 29
<212> TYPE: DNA
<213> ORGANISM: Artificial Sequence
<220> FEATURE:
<223> OTHER INFORMATION: primer

<400> SEQUENCE: 33
cgcctcgagt tttaagtttg caaaagcct                                            29

<210> SEQ ID NO 34
<211> LENGTH: 25
<212> TYPE: DNA
<213> ORGANISM: Artificial Sequence
<220> FEATURE:
<223> OTHER INFORMATION: primer

<400> SEQUENCE: 34
cccccatggt gcgttgttta gcact                                                25

<210> SEQ ID NO 35
<211> LENGTH: 25
<212> TYPE: DNA
<213> ORGANISM: Artificial Sequence
<220> FEATURE:
<223> OTHER INFORMATION: primer

<400> SEQUENCE: 35
ccgctcgagg ccataaattg ttcct                                                25

<210> SEQ ID NO 36
<211> LENGTH: 27
<212> TYPE: DNA
<213> ORGANISM: Artificial Sequence
<220> FEATURE:
<223> OTHER INFORMATION: primer

<400> SEQUENCE: 36
cgcccatggt gtcattacgc attaaac                              27

<210> SEQ ID NO 37
<211> LENGTH: 28
<212> TYPE: DNA
<213> ORGANISM: Artificial Sequence
<220> FEATURE:
<223> OTHER INFORMATION: primer

<400> SEQUENCE: 37
ccgctcgagg cccatacgat agttcggt                             28

<210> SEQ ID NO 38
<211> LENGTH: 27
<212> TYPE: DNA
<213> ORGANISM: Artificial Sequence
<220> FEATURE:
<223> OTHER INFORMATION: primer

<400> SEQUENCE: 38
ccgccatggt gcaacaacac aatctct                              27

<210> SEQ ID NO 39
<211> LENGTH: 28
<212> TYPE: DNA
<213> ORGANISM: Artificial Sequence
<220> FEATURE:
<223> OTHER INFORMATION: primer

<400> SEQUENCE: 39
ccgctcgaga attcgctcaa aaccagct                             28

<210> SEQ ID NO 40
<211> LENGTH: 28
<212> TYPE: DNA
<213> ORGANISM: Artificial Sequence
<220> FEATURE:
<223> OTHER INFORMATION: primer

<400> SEQUENCE: 40
ccgccatggt gcaaaaacag attgaaat                             28

<210> SEQ ID NO 41
<211> LENGTH: 29
<212> TYPE: DNA
<213> ORGANISM: Artificial Sequence
<220> FEATURE:
<223> OTHER INFORMATION: primer

<400> SEQUENCE: 41
cccctcgagt tcttcaaaat accccatat                            29

<210> SEQ ID NO 42
<211> LENGTH: 27
<212> TYPE: DNA
<213> ORGANISM: Artificial Sequence
<220> FEATURE:
<223> OTHER INFORMATION: primer

```
<400> SEQUENCE: 42
gcgccatggt gaatcaaaat ctaattg                                        27

<210> SEQ ID NO 43
<211> LENGTH: 27
<212> TYPE: DNA
<213> ORGANISM: Artificial Sequence
<220> FEATURE:
<223> OTHER INFORMATION: primer

<400> SEQUENCE: 43
cgcctcgagt tcaaacaatt ccttcat                                        27

<210> SEQ ID NO 44
<211> LENGTH: 27
<212> TYPE: DNA
<213> ORGANISM: Artificial Sequence
<220> FEATURE:
<223> OTHER INFORMATION: primer

<400> SEQUENCE: 44
gcgccatggt gaaacttaca tcgaaag                                        27

<210> SEQ ID NO 45
<211> LENGTH: 26
<212> TYPE: DNA
<213> ORGANISM: Artificial Sequence
<220> FEATURE:
<223> OTHER INFORMATION: primer

<400> SEQUENCE: 45
gagctcgagt tgattaacta ataaat                                         26

<210> SEQ ID NO 46
<211> LENGTH: 27
<212> TYPE: DNA
<213> ORGANISM: Artificial Sequence
<220> FEATURE:
<223> OTHER INFORMATION: primer

<400> SEQUENCE: 46
gcgccatggt gaaaaaaaca cttgcag                                        27

<210> SEQ ID NO 47
<211> LENGTH: 27
<212> TYPE: DNA
<213> ORGANISM: Artificial Sequence
<220> FEATURE:
<223> OTHER INFORMATION: primer

<400> SEQUENCE: 47
cgcctcgagg taaacgcgta aacctac                                        27

<210> SEQ ID NO 48
<211> LENGTH: 27
<212> TYPE: DNA
<213> ORGANISM: Artificial Sequence
<220> FEATURE:
<223> OTHER INFORMATION: primer

<400> SEQUENCE: 48
cgcccatgga aacgtattca ttattac                                        27

<210> SEQ ID NO 49
<211> LENGTH: 27
```

```
<212> TYPE: DNA
<213> ORGANISM: Artificial Sequence
<220> FEATURE:
<223> OTHER INFORMATION: primer

<400> SEQUENCE: 49
cgcctcgagc tcacattgaa ttattac                                                27
```